US 8,922,690 B2

(12) United States Patent
Nakata

(10) Patent No.: US 8,922,690 B2
(45) Date of Patent: Dec. 30, 2014

(54) IMAGE SENSOR, IMAGING APPARATUS AND LIVE BODY IMAGING APPARATUS

(75) Inventor: Masashi Nakata, Kanagawa (JP)

(73) Assignee: Sony Corporation (JP)

( * ) Notice: Subject to any disclaimer, the term of this patent is extended or adjusted under 35 U.S.C. 154(b) by 48 days.

(21) Appl. No.: 13/587,108

(22) Filed: Aug. 16, 2012

(65) Prior Publication Data

US 2013/0050562 A1    Feb. 28, 2013

(30) Foreign Application Priority Data

Aug. 25, 2011   (JP) ................................. 2011-183303

(51) Int. Cl.
| | |
|---|---|
| H04N 3/14 | (2006.01) |
| H04N 5/235 | (2006.01) |
| H01L 31/00 | (2006.01) |
| H04N 5/3745 | (2011.01) |
| G02B 5/20 | (2006.01) |
| H01L 27/146 | (2006.01) |
| H04N 5/355 | (2011.01) |
| H04N 9/04 | (2006.01) |
| A61B 5/1455 | (2006.01) |

(52) U.S. Cl.
CPC ............ *H04N 5/37457* (2013.01); *G02B 5/201* (2013.01); *H01L 27/14621* (2013.01); *H01L 27/14627* (2013.01); *H04N 5/35554* (2013.01); *H04N 5/3745* (2013.01); *H04N 9/045* (2013.01); *A61B 5/14552* (2013.01); *A61B 2562/0233* (2013.01); *A61B 2562/046* (2013.01)
USPC ......... 348/308; 348/294; 348/229.1; 348/336; 348/272; 359/589; 359/583; 359/891; 257/291; 257/294; 257/440; 250/208.1; 250/214 R

(58) Field of Classification Search
CPC ........... H04N 3/14; H04N 5/235; H03M 1/12; H01L 27/00; H01L 40/14; H01L 31/00; H01L 31/062; G02B 5/28; G02B 1/10; G02B 5/22
USPC .............. 348/272, 280, 336, 294–324, 229.1; 250/208.1, 214, 214 R; 257/291, 292, 257/440, 294; 359/589, 583, 891; 341/155
See application file for complete search history.

(56) References Cited

U.S. PATENT DOCUMENTS

| | | | | |
|---|---|---|---|---|
| 2008/0012969 | A1* | 1/2008 | Kasai et al. | 348/266 |
| 2010/0013969 | A1* | 1/2010 | Ui | 348/294 |
| 2010/0177226 | A1* | 7/2010 | Itonaga et al. | 348/300 |
| 2010/0276573 | A1 | 11/2010 | Duerksen | |
| 2011/0141569 | A1 | 6/2011 | Wehner | |

FOREIGN PATENT DOCUMENTS

EP     2146498     1/2010

OTHER PUBLICATIONS

Extended Search Report for European Patent Application No. 12005931.6, dated Dec. 6, 2012, 6 pages.

* cited by examiner

*Primary Examiner* — Lin Ye
*Assistant Examiner* — Marly Camargo
(74) *Attorney, Agent, or Firm* — Sheridan Ross P.C.

(57) ABSTRACT

An image sensor including a pixel unit, the pixel unit including a photodiode, a first color filter and a second color filter each disposed in a different position on a plane above the photodiode, and a first on-chip lens disposed over the first color filter and a second on-chip lens disposed over the second color filter.

19 Claims, 20 Drawing Sheets

FIG. 1
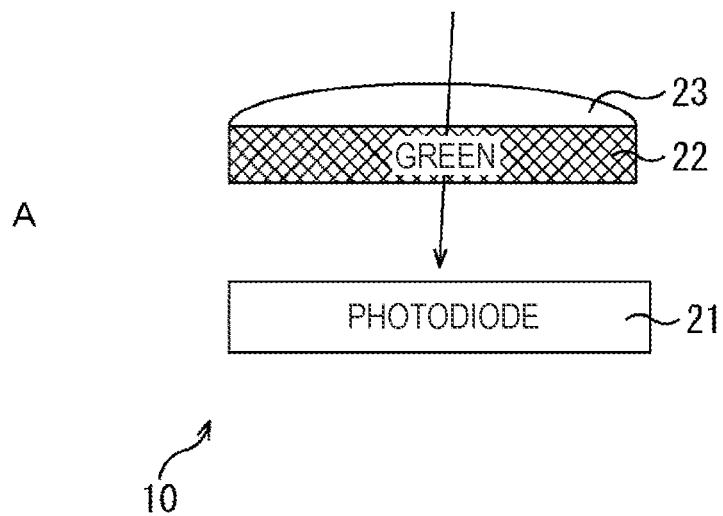
A
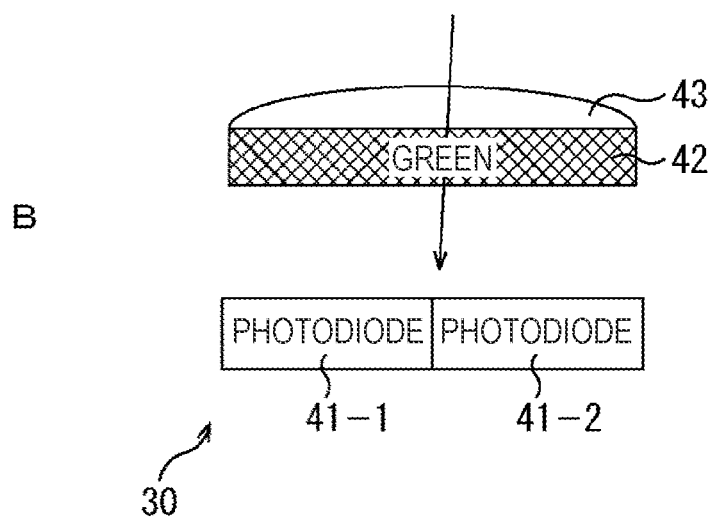
B

FIG. 2
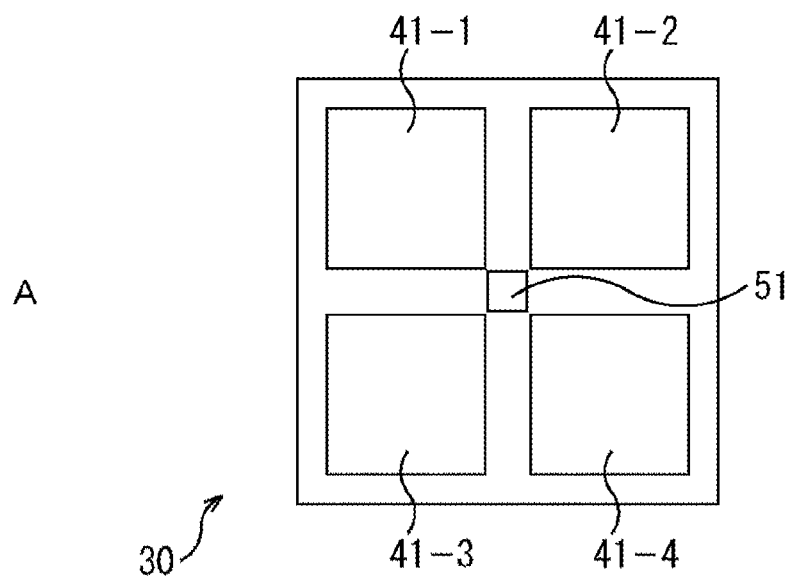
A
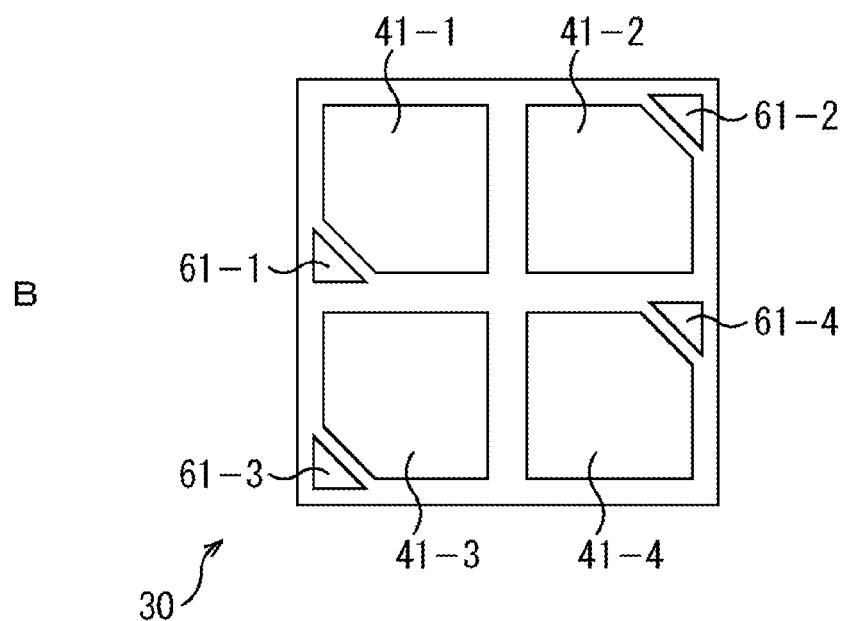
B

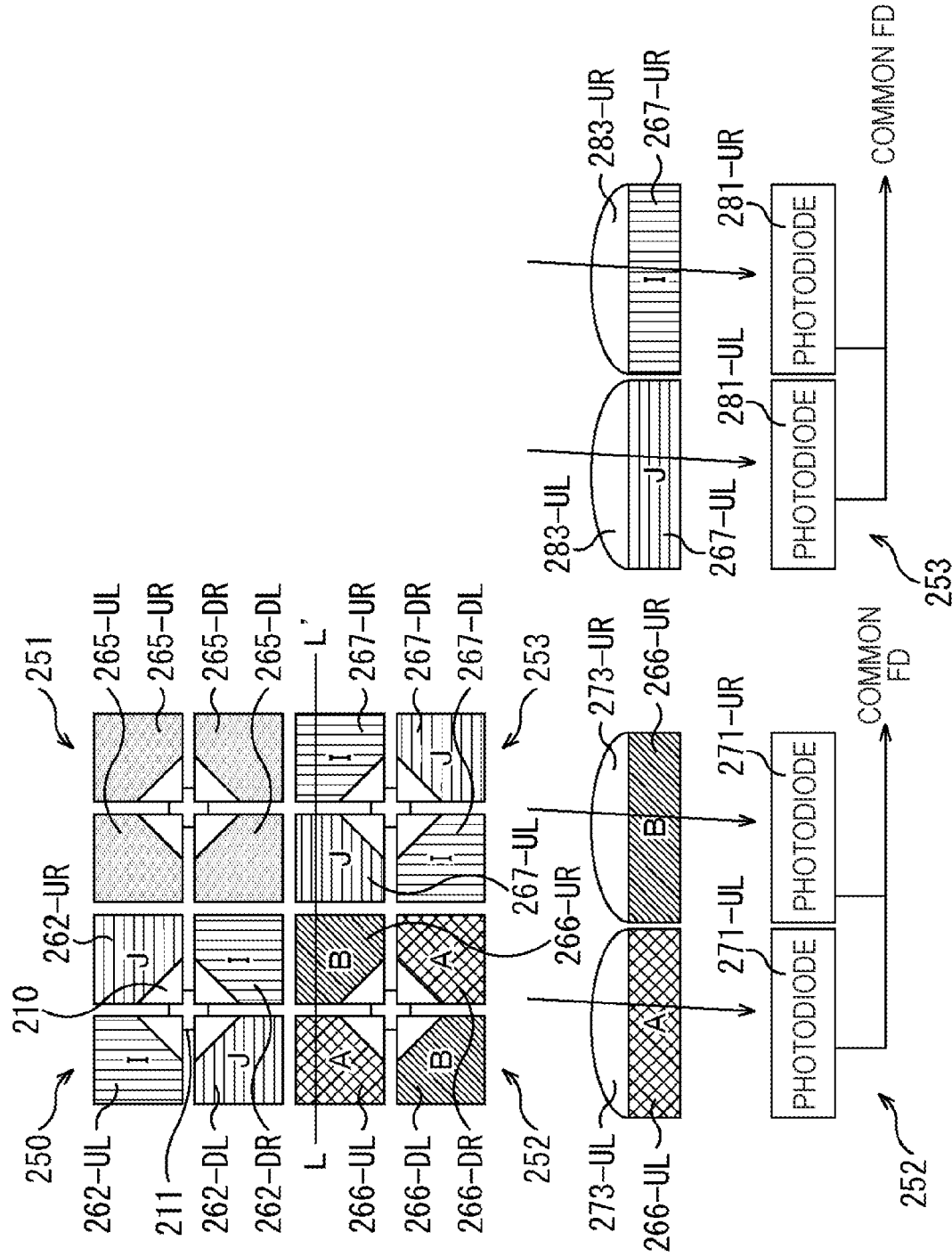

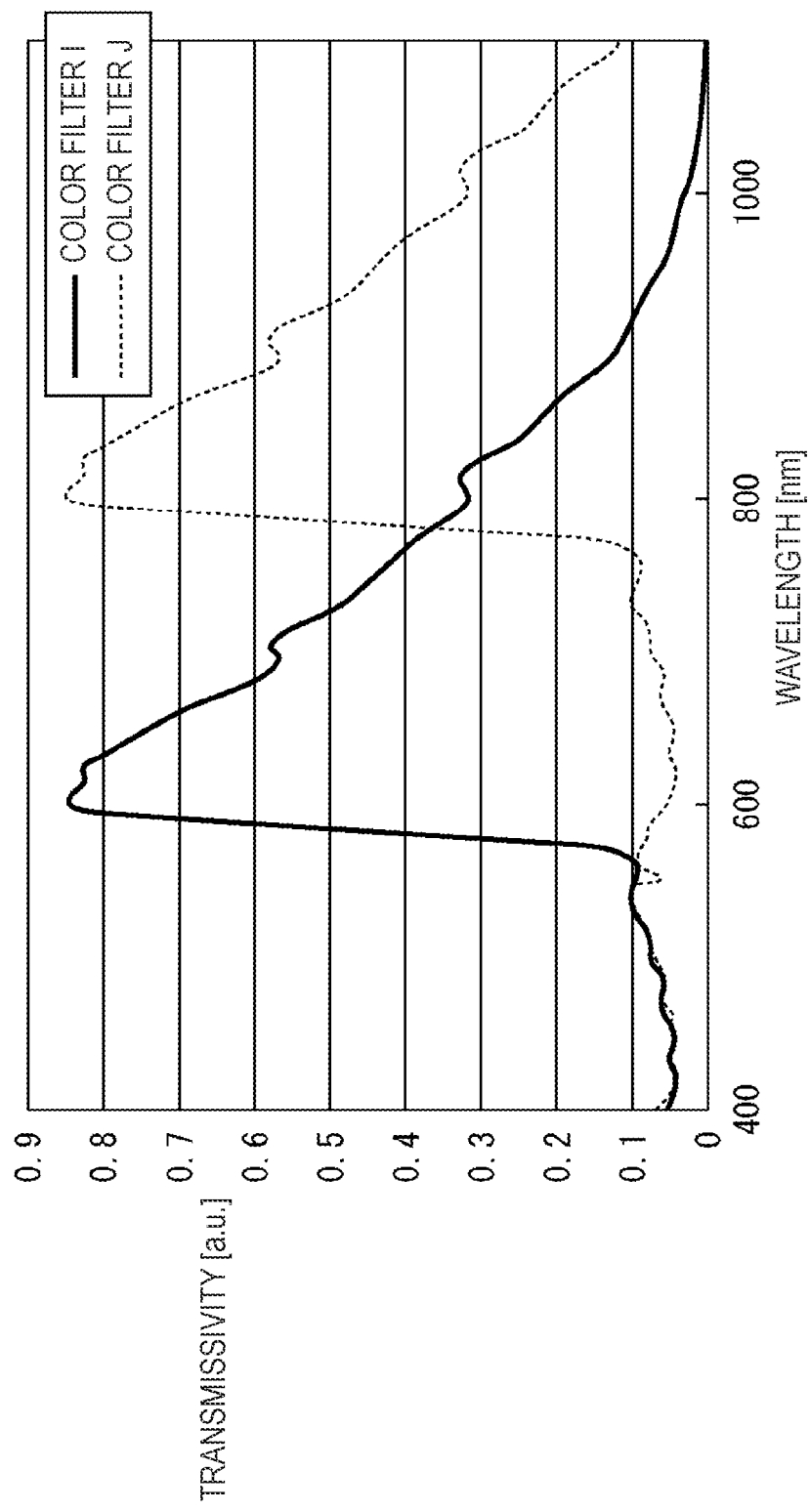

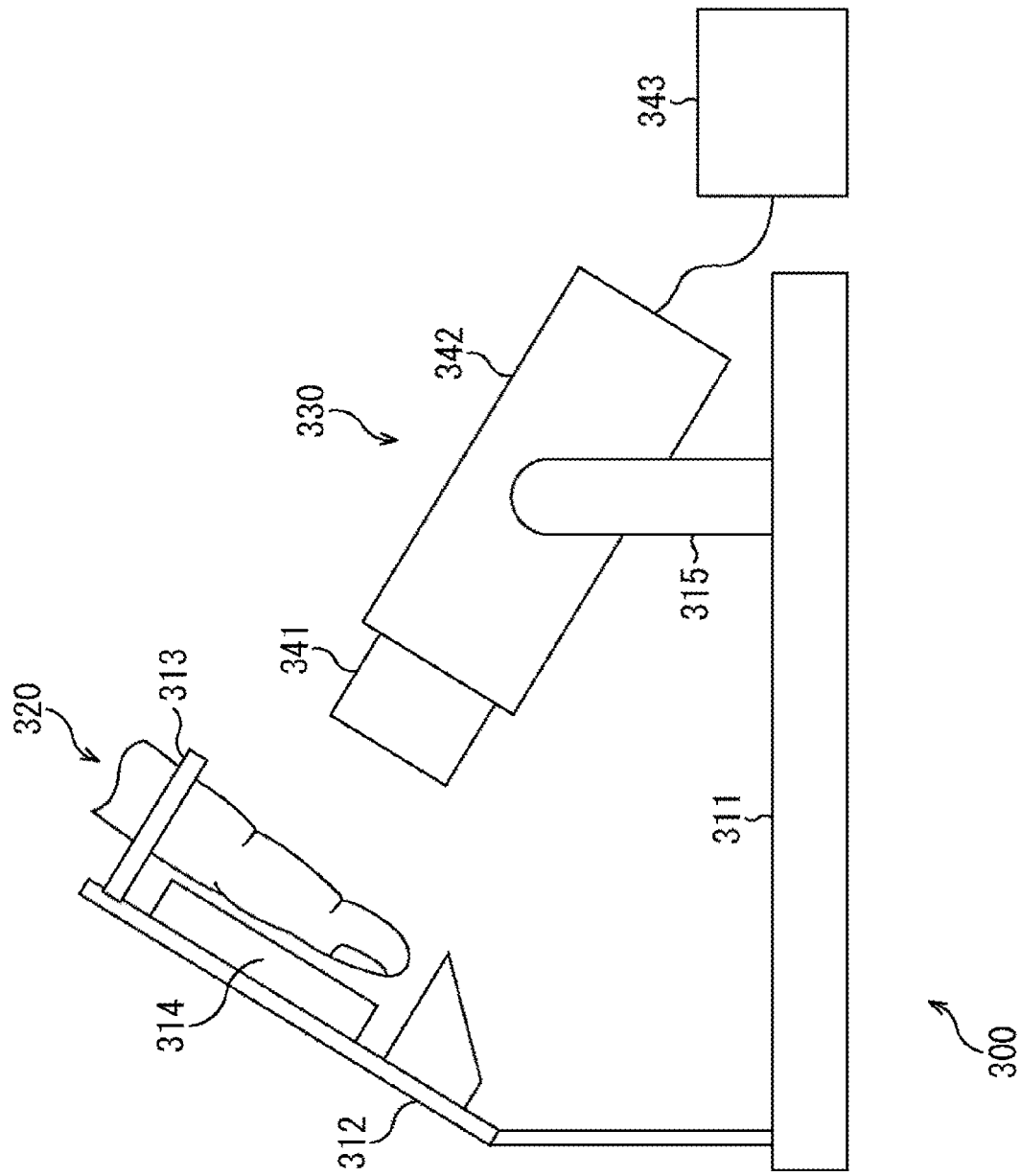

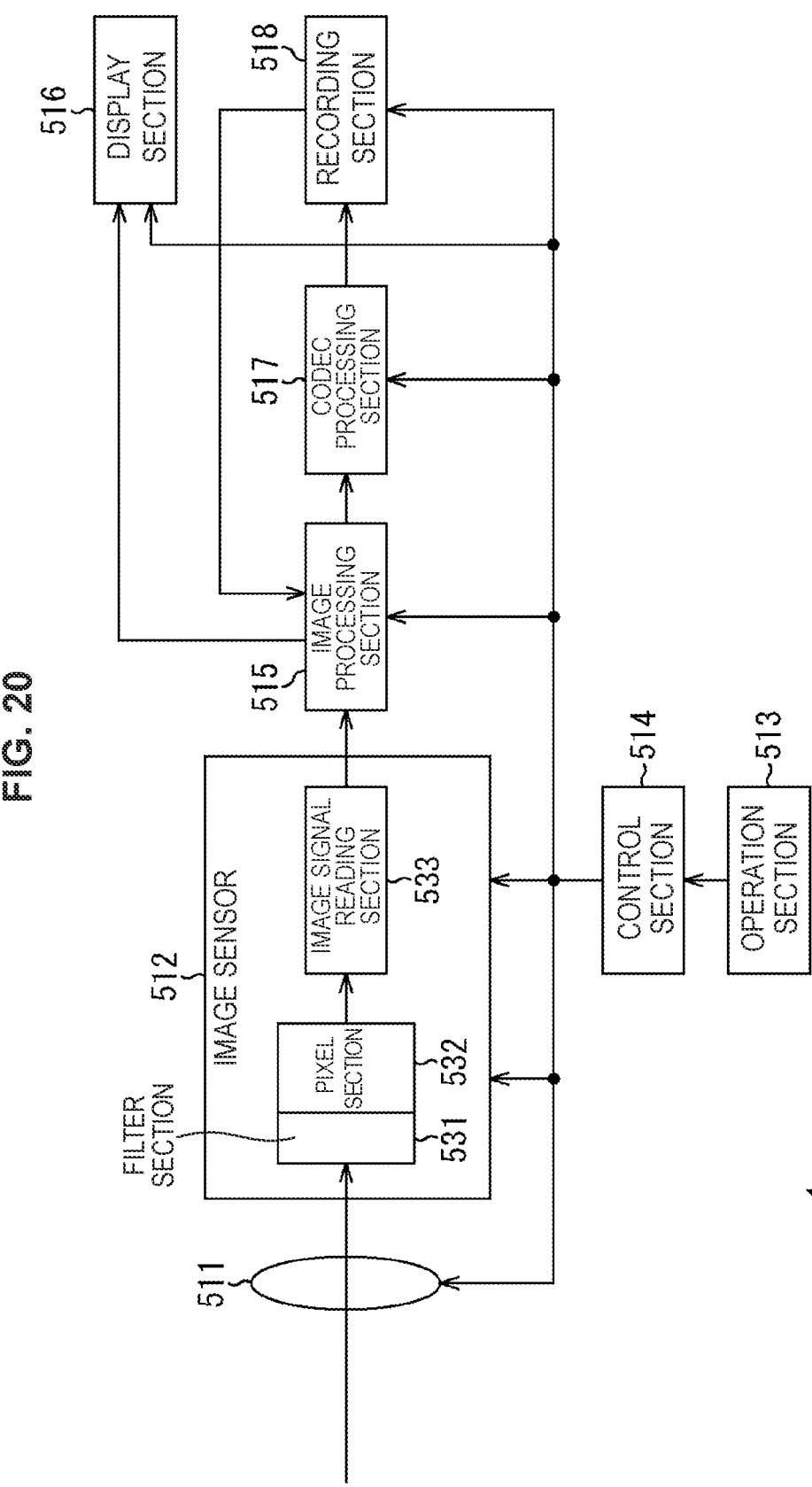

IMAGE SENSOR, IMAGING APPARATUS AND LIVE BODY IMAGING APPARATUS

BACKGROUND

The present technology relates to an image sensor, an imaging apparatus and a live body imaging apparatus, in particular to an image sensor which is capable of creating optimal spectral characteristic, an imaging apparatus and a live body imaging apparatus.

In a known image sensor such as CMOS (Complementary Metal Oxide Semiconductor) image sensor, generally, a pixel is configured including, with respect to a single photodiode, a single color filter and a single on-chip lens are disposed (refer to, for example, Japanese Unexamined Patent Application Publication No. 2010-232595). On the other hand, there is another known pixel is configured including, for example, with respect to plural photodiodes, a single color filter is disposed, and outputs from the plural photodiodes are added (refer to, for example, Japanese Unexamined Patent Application Publication No. 2010-28423).

SUMMARY

However, in the pixels which have a configuration taught by Japanese Unexamined Patent Application Publications No. 2010-232595 and Japanese Unexamined Patent Application Publication No. 2010-28423, the spectral characteristic of the light concentrated on the photodiode depends on the spectral characteristic of the color filter disposed above the photodiode. Therefore, in order to improve the S/N ratio (Signal to Noise Ratio) and the color reproducibility, development of a new color filter is desired. However, for developing a new color filter, enormous time and cost is necessary. Also, even when a material for new color filter is developed, it is difficult to obtain optimal spectral characteristic of the light concentrated on the photodiodes of the respective pixels suitable for the application. Under such circumstances, a technique to create optimal spectral characteristic, which does not depend on only the development of material for color filter, is desired.

The present technology has been proposed in view of the above circumstances to create an optimal spectral characteristic.

An image sensor an aspect of the present technology includes a pixel unit, which has a photodiode; a first color filter and a second color filter each disposed in a different position on a plane above the photodiode; and a first on-chip lens disposed over the first color filter and a second on-chip lens disposed over the second color filter.

Each of the first color filter and the second color filter may have a spectral characteristic different from each other.

The pixel unit may output an electrical signal of a level corresponding to a composition result of the spectral characteristics of the first color filter and the second color filter.

The photodiode may include a first photodiode disposed below the first color filter and a second photodiode disposed below the second color filter, and electrical signals output from the pixel unit having levels corresponding to the respective spectral characteristics of the first color filter and the second color filter may be added.

The pixel unit may further include a common floating diffusion that adds electrical signals output from each of the first photodiode and the second photodiode.

Each of the electrical signals output from the first photodiode and the second photodiode may be amplified by an individually preset gain.

Each of the first photodiode and the second photodiode may be individually preset with a charge accumulating time.

Each of the first color filter and the second color filter may have a characteristic to transmit infrared light.

The pixel unit may include a group of color filters which includes one or more color filters in addition to the first color filter and the second color filter, and a group of on-chip lenses which includes one or more on-chip lenses in addition to the first on-chip lens and the second on-chip lens, the one or more on-chip lenses being disposed over the one or more color filters in addition to the first color filter and the second color filter.

The pixel unit may output an electrical signal of a level corresponding to a composition result of the respective spectral characteristics of the color filter group.

The photodiode may be constituted of a photodiode group each disposed below the color filter group, and electrical signals output from the pixel unit each having a level corresponding to a spectral characteristic of the color filter group may be added.

The pixel unit may further include a common floating diffusion that adds the electrical signals each output from the photodiode groups.

Each of the electrical signals output from the photodiode groups may be amplified by an individually preset gain.

Each photodiode group may be individually preset with a charge accumulating time.

Each of the color filter groups may have a characteristic to transmit infrared light.

A waveguide may be formed above the photodiode.

The photodiode may have a plurality of output modes which are selectively switchable through an inner or outer control of the image sensor.

An imaging apparatus of an aspect of the present technology is mounted with an image sensor including a pixel unit, the pixel unit includes a photodiode; a first color filter and a second color filter each disposed in a different position on a plane above the photodiode; and a first on-chip lens disposed over the first color filter and a second on-chip lens disposed over the second color filter.

A live body imaging apparatus of an aspect of the present technology includes an imaging apparatus mounted with an image sensor including a pixel unit, the pixel unit includes a photodiode; a first color filter and a second color filter each disposed in a different position on a plane above the photodiode; and a first on-chip lens disposed over the first color filter and a second on-chip lens disposed over the second color filter, wherein, the imaging apparatus takes a picture of a live body as an object.

In the image sensor of one aspect of the present technology, a pixel unit is provide in which a photodiode; a first color filter and a second color filter each disposed in a different position on a plane above the photodiode; and a first on-chip lens disposed over the first color filter and a second on-chip lens disposed over the second color filter are included.

In an imaging apparatus of one aspect of the present technology, an image sensor including a pixel unit is mounted, in which a photodiode; a first color filter and a second color filter each disposed in a different position on a plane above the photodiode; and a first on-chip lens disposed over the first color filter and a second on-chip lens disposed over the second color filter are included.

In a live body imaging apparatus of one aspect of the present technology, an imaging apparatus is mounted with an image sensor including a pixel unit, in which the pixel unit includes a photodiode; a first color filter and a second color filter each disposed in a different position on a plane above the photodiode; and a first on-chip lens disposed over the first color filter and a second on-chip lens disposed over the second color filter, wherein a picture of a live body as an object is taken by the imaging apparatus.

As described above, according to the present technology, an optimal spectral characteristic can be created.

BRIEF DESCRIPTION OF THE DRAWINGS

FIG. 1 is a cross-sectional view of a pixel unit of a general configuration;
FIG. 2 is a top view of an N-divided pixel unit;
FIG. 17 illustrates an example of a configuration of an N-divided pixel unit of a configuration of the present technology in which an infrared color filter is disposed;
FIG. 18 is a diagram showing spectral characteristics of an I-color filter and a J-color filter;
FIG. 19 illustrates an example of a configuration of a live body information obtaining system;
and
FIG. 20 is a block diagram showing an example of a configuration of an imaging apparatus to which the present technology is applied.

DETAILED DESCRIPTION OF THE EMBODIMENTS

Figure 3:
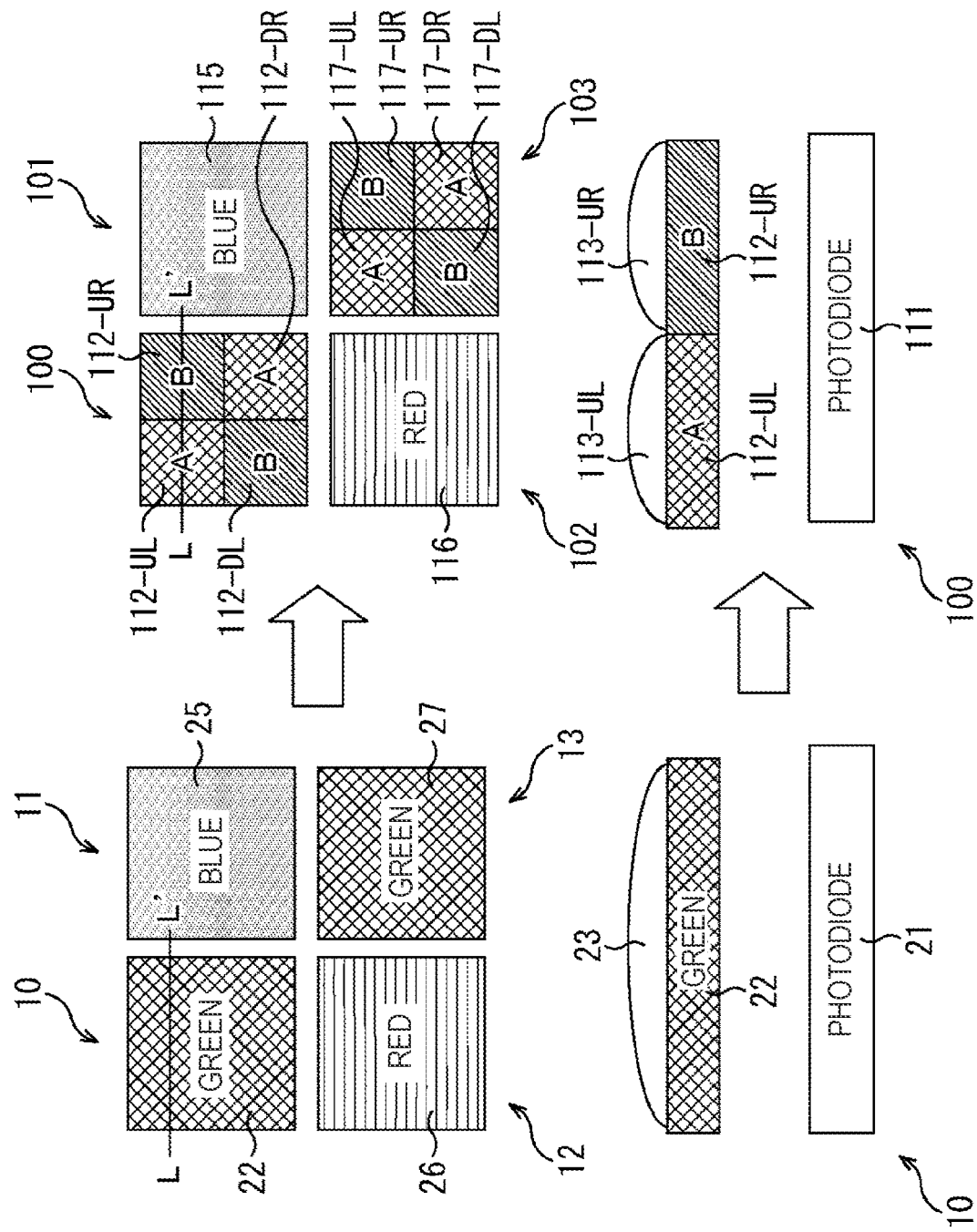
FIG. 3 illustrates an example of a configuration of a single pixel unit configured by applying the technique of the present technology.

Embodiments of the present technology will be described below.

First of all, a description will be given on a general pixel which configures an image sensor. Hereinafter, the following description will made while assuming that the acceptance surface of an image sensor is the upper surface, the surface opposite to the acceptance surface is the bottom surface; and direction parallel to a normal of the acceptance surface is a vertical direction, and a direction parallel to the acceptance surface is a lateral direction.

[General Configuration of a Pixel]

FIG. 1 is a cross-sectional view of a pixel unit of a general configuration.

The pixel unit means a structure which includes several composing elements, in addition to a photodiode as a pixel, a color filter, an on-chip lens and the like. Typical pixel unit includes the following two types.

One type is a pixel unit which has single photodiode as the pixel. Such pixel unit will be referred below to as single pixel unit. The other type is a pixel unit which has N (N is an integer greater than 2) of photodiodes as the pixels. Such pixel unit will be referred to as N-divided pixel unit.

A single pixel unit 10 shown in FIG. 1A is configured including, with respect to one single photodiode 21, a green color filter 22 and an on-chip lens 23 which are laminated in this order from the bottom. Although not shown in the figure, between the photodiode 21 and green color filter 22, a light transmissive planarization film or the like may be disposed.

A ray of light entered into the on-chip lens 23 passes through the green color filter 22 and is focused on the photodiode 21 and finally enters into the photodiode 21. In more precisely, in the green color filter 22, in the light coming out from the on-chip lens 23, only the light having specific wavelength bands (i.e. green wavelength bands) passes through the green color filter 22 and enters into the photodiode 21. The photodiode 21 outputs an electrical signal of a level corresponding to the amount of entered light; i.e. the amount of received light. Here note that, for the convenience of explanation, although the color filter disposed in the single pixel unit 10 is the green color filter 22, but the color of the color filter is not particularly limited thereto.

An N(=2)-divided pixel unit 30 shown in FIG. 1B is configured including, with respect to a of pair neighboring two photodiodes 41-1 and 41-2, a green color filter 42 and an on-chip lens 43 are laminated in this order from the bottom. The number of the photodiodes disposed in the N-divided pixel unit is not limited to two.

A lay of light entering the on-chip lens 43 passes through the green color filter 42 and is focused on the photodiodes 41-1 and 41-2, and enters thereinto. In more precisely, in the green color filter 42, in the light coming out of the on-chip lens 43, only the light having specific wavelength bands (i.e. green wavelength bands) passes therethrough and enters into the photodiodes 41-1 and 41-2. Each of the photodiodes 41-1 and 41-2 outputs an electrical signal of a level corresponding to the amount of entered light; i.e. the amount of received light respectively.

In the N-divided pixel unit 30, an electrical signal of a level equivalent to the sum of every levels corresponding to the amount of light received by each of N photodiodes. Referring to FIG. 2, a description on the output from the N-divided pixel unit 30 will be made.

[Output from the N-Divided Pixel Unit]

FIG. 2 is a top view of an N-divided pixel unit when N=4. Two techniques are available for adding each of the electrical signals from the N photodiodes. FIG. 2A is a top view of an N-divided pixel unit to which a first adding technique is applied. FIG. 2B is top view of an N-divided pixel unit to which a second adding technique is applied. In the top views in FIG. 2, the on-chip lens 43 and the green color filter 42 are not shown.

As shown in FIG. 2A, in the N-divided pixel unit 30 to which the first adding technique is applied, photodiodes 41-1 to 41-4 are disposed. In a central position of the photodiodes 41-1 to 41-4, a common floating diffusion (hereinafter, referred to as common FD) section 51 is disposed.

According to the first adding technique, the electrical signals from the photodiodes 41-1 to 41-4, each having a level corresponding to the amount of received light, is transferred to the common FD section 51 respectively. The common FD section 51 adds every electrical signals and outputs an electrical signal of a level; i.e. the sum of each levels. Thus, in the first adding technique, each of the electrical signals from the N photodiodes are summed and then output therefrom.

Also, in the N-divided pixel unit 30 to which the second adding technique is applied, photodiodes 41-1 to 41-4 are dispose same as those in FIG. 2A as shown in FIG. 2B. Each of the photodiodes 41-1 to 41-4 is provided with an individual floating diffusion (hereinafter, referred to as individual FD) section 61-1 to 61-4 respectively.

According to the second adding technique, each of the electrical signals of a level corresponding to the amount of light received by the respective photodiodes 41-1 to 41-4 is transferred to each of the individual FD sections 61-1 to 61-4. All of the electrical signals are separately output from the individual FD sections 61-1 to 61-4, and are added in an image signal reading section (not shown). Thus, in the second adding technique, the electrical signals from each of the N photodiodes is summed after being output from the individual FD sections 61-1 to 61-4.

In the N-divided pixel unit, even when either the first adding technique or the second adding technique is applied thereto, since an electrical signal of a level, in which all levels corresponding to the amount of received light from each of the N photodiodes are summed ultimately resulting in one electrical signal from one pixel, and is output therefrom.

As described above, both of the single pixel unit 10 of a general configuration and the N-divided pixel unit 30 are provided with one color filter and a single on-chip lens.

The spectral characteristic of the light focused on each photodiode depend on the spectral characteristics of the color filters disposed on the respective photodiodes. Therefore, for improving the S/N ratio and the color reproducibility, a new color filter is desired to be developed. However, as described above, to develop a new color filter, an enormous time and cost are necessary. Also, even if a new material for color filter is developed, it is difficult to optimize the spectral characteristic of the light focused on the photodiode of each pixel to be suitable to the purpose of application.

On the other hand, an image sensor which has an emerald pixel with enhanced color reproducibility is known. Contrarily to the known image sensors which have three primary color pixels of R-pixel, G-pixel and B-pixel, the image sensor having the emerald pixel is an image sensor having a configuration of four primary color pixels, in which the ratio of G-pixels is reduced but equivalent amount of emerald pixels are added. However, compared to known image sensors, in the image sensor having emerald pixels, since G-pixels are reduced as described above, the resolution may be deteriorated proportionally.

Also, there is known a technique to estimate right source based on pixel values of R-pixel, G-pixel and B-pixel. However, new light sources such as white LED are increasingly used. Estimation of the light source is getting difficult.

The inventor of the technology has developed a technique to laminate plural color filters and plural on-chip lenses in deferent positions on a plane of one pixel unit. Here, the position on a plane means a position on a two-dimensional plane parallel to the acceptance surface of the image sensor, which is a position determined by coordinates indicating pixel position on the image sensor. Hereinafter, such technique will be referred to as technique of the present technology. By applying the technique of the present technology, an optimal spectral characteristic can be created.

Figure 4:
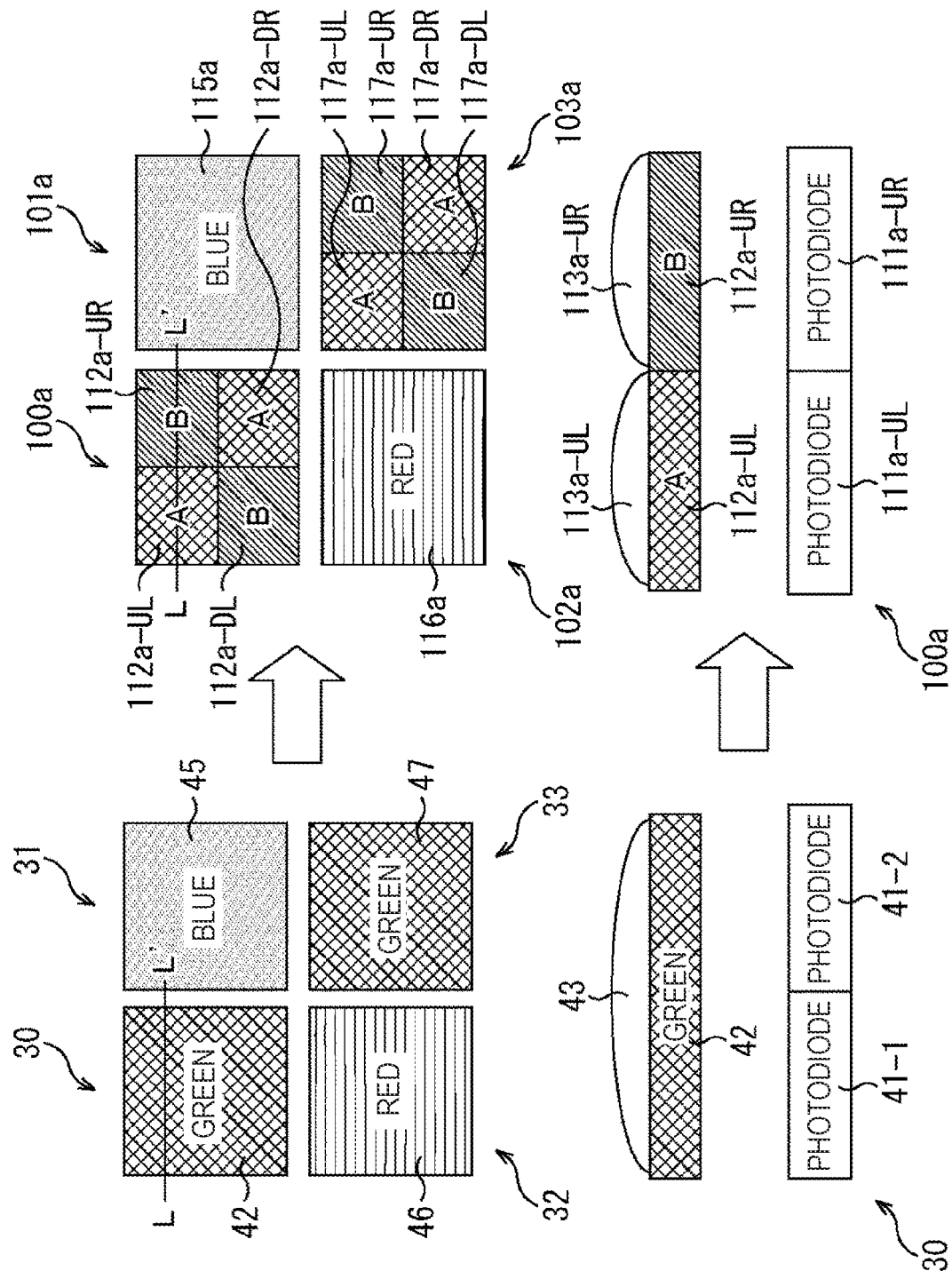
FIG. 4 illustrates an example of a configuration of an N-divided pixel unit configured by applying the technique of the present technology.

Referring to FIG. 3 and FIG. 4, a description will be made on a single pixel unit and an N-divided pixel unit which are configured by applying the technique of the present technology.

[Single Pixel Unit Configured by Applying the Technique of the Present Technology]

FIG. 3 is an illustration showing an example of the configuration of a single pixel unit configured by applying the technique of the present technology. At the left side in FIG. 3, a single pixel unit 10 of a general configuration is shown. At the right side in FIG. 3, a single pixel unit 100 configured by applying the technique of the present technology is shown.

At the upper-left in FIG. 3, a top view of a group of neighboring four single pixel units 10 to 13 of a general configuration is shown. Note that the on-chip lens is omitted in the top views shown in FIG. 3 or later. The single pixel unit 10 is disposed with a green color filter 22. A single pixel unit 11 is disposed with a blue color filter 25. A single pixel unit 12 is disposed with a red color filter 26. A single pixel unit 13 is disposed with a green color filter 27.

A cross-sectional view of the single pixel unit 10 of a general configuration taken along a line L-L' is shown at lower-left in FIG. 3. As described referring to FIG. 1A, the single pixel unit 10 of a general configuration is configured including, with respect to a single photodiode 21, a single green color filter 22 and a single on-chip lens 23 being laminated in this order from the bottom.

By applying the technique of the present technology to the single pixel units 10 and 13 of a general configuration, single pixel units 100 and 103 of configuration shown at the right side in FIG. 3 (hereinafter, referred to as single pixel units 100 and 103 of a configuration of the present technology) are obtained. That is, the single green color filters 22 and 27 disposed on the single pixel units 10 and 13 are divided into four respectively, and the 4-divided green color filters 22 and 27 are replaced with A-color filters and B-color filters of a number of ratio 1:1 (i.e. two each). With this, plural color filters are disposed in different positions on a plane in one pixel unit.

A top view of a group of the single pixel units 100 and 103 of a configuration of the present technology and the single pixel units 101 and 102 of a general configuration is shown in upper-right of FIG. 3.

The single pixel unit 100 of a configuration of the present technology is disposed with A-color filters 112-UR and 112-DR and B-color filters 112-UR and 112-DL. Here, the A-color filter means a filter which transmits only the light of wavelength bands of A-color in the light coming out of the on-chip lens. On the other hand, the B-color filter means a filter which transmits only the light of wavelength bands of B-color different from the wavelength bands of A-color in the light coming out of the on-chip lens. Both of the A-color filter and the B-color filter are replaced with general green color filters respectively. Therefore, the A-color filter and the B-color filter are color filters which transmit the light of wavelength bands in an arbitrary range (i.e., a first range and a second range different from that) within the wavelength bands that the general green color filter transmits the light (approximately, a range of 500 to 570 nm).

Likewise, the single pixel unit 103 of a configuration of the present technology is dispose with A-color filters 117-UL and 117-DR, and B-color filters 117-UR and 117-DL. That is, the single pixel units 100 and 103 of a configuration of the present technology are disposed with the A-color filters and the B-color filters of a number with the ratio 1:1 (i.e. two each).

Same as the single pixel unit 11 of a general configuration shown at the upper-left in FIG. 3, the single pixel unit 101 of a general configuration is disposed with the blue color filter 115. Also, the single pixel unit 102 of a general configuration is disposed with a red color filter 116 same as the single pixel unit 12 of a general configuration shown at the upper-left in FIG. 3.

A cross-sectional view of the single pixel unit 100 of a configuration of the present technology taken along a line L-L' is shown at the lower-right in FIG. 3.

The single pixel unit 100 of a configuration of the present technology is configured including, with respect to the single photodiode 111, a pair of the A-color filter 112-UL and the B-color filter 112-UR, a pair of an on-chip lens 113-UL and an on-chip lens 113-UR being laminated in this order from the bottom. That is, above the A-color filter 112-UL, the on-chip lens 113-UL is disposed; and above the B-color filter 112-UR, the on-chip lens 113-UR is disposed.

As described above, in the example of FIG. 3, in the single pixel unit 100 of a configuration of the present technology, as for the color filter disposed over the single photodiode 111, 2 types of color filters such as the A-color filters 112-UR and 112-DR and the B-color filters 112-UR and 112-DL are employed, and color filters of identical type are disposed on a diagonal line. However, the color filter employed for the single pixel unit of a configuration of the present technology is not particularly limited to the example in FIG. 3, but plural color filters of two or more types may be arbitrary employed.

[N-Divided Pixel Unit Configured by Applying the Technique of The Present Technology]

FIG. 4 illustrates an example of a configuration of an N-divided pixel unit configured by applying the technique of the present technology. The N-divided pixel unit 30 of a general configuration is shown at the left side in FIG. 4; an N-divided pixel unit 100a configured by applying the technique of the present technology is shown at the right side in FIG. 4.

A top view of a group of neighboring four N-divided pixel units 30 to 33 of a general configuration is shown at the upper-left in FIG. 4. The N-divided pixel unit 30 is disposed with the green color filter 42. The N-divided pixel unit 31 is disposed with the green color filter 45. The N-divided pixel unit 32 is disposed with the green color filter 46. The N-divided pixel unit 33 is disposed with the green color filter 47.

A cross-sectional view of the N-divided pixel unit 30 of a general configuration taken along line L-L' is shown at the lower-left in FIG. 4. As described referring to FIG. 1B, the N-divided pixel unit 30 of a general configuration is configured including, with respect to the a pair of neighboring two photodiodes 41-1 and 41-2, a single green color filter 42 and a single on-chip lens 43 being laminated in this order from the bottom.

By applying the technique of the present technology to the N-divided pixel units 3 and 33 of a general configuration, N-divided pixel units 100a and 103a of a configuration of the present technology shown at the right side in FIG. 4 are obtained. That is, the single green color filters 42 and 47 disposed on the N-divided pixel units 30 and 33 are divided into four respectively; the four divided green color filters 42 and 47 are replaced with the A-color filter and the B-color filter of a number with the ratio 1:1 (i.e. two each) respectively. With this, plural color filters are disposed in different positions on a plane within one pixel unit.

A top view of a group of the N-divided pixel units 100a and 103a of a configuration of the present technology and the N-divided pixel units 101a and 102a of a general configuration is shown at the upper-right in FIG. 4.

The N-divided pixel unit 100a of a configuration of the present technology is disposed with A-color filters 112a-UL and 112a-DR and B-color filters 112a-UR and 112a-DL. Likewise, the single pixel unit 103 of a configuration of the present technology is disposed with A-color filters 117a-UL and 117a-DR and B-color filters 117a-UR and 117a-DL. That is, the N-divided pixel units 100a and 103a of a configuration of the present technology is disposed with the A-color filters and the B-color filters of a number with the ratio of 1:1 (i.e. two each).

Same as the N-divided pixel unit 31 of a general configuration shown at the upper-left in FIG. 4, the N-divided pixel unit 101a of a general configuration is disposed with a blue color filter 115a. Also, same as the N-divided pixel unit 32 of a general configuration shown at the upper-left in FIG. 4, the N-divided pixel unit 102a of a general configuration, is disposed with a red color filter 116a.

A cross-sectional view of the N-divided pixel unit 100a of a configuration of the present technology taken along a line L-L' is shown at the lower-right in FIG. 4.

The N-divided pixel unit 100a of a configuration of the present technology is configured including, with respect to a pair of neighboring two photodiodes 111a-UL and 111a-UR, a pair of an A-color filters 112a-UL and a B-color filters 112a-UR, and a pair of an on-chip lens 113a-UL and an on-chip lens 113a-UR being laminated in this order from the bottom. That is, the photodiode 111a-UL, the A-color filters 112a-UL and the on-chip lens 113a-UL are disposed in this order from the bottom; and the photodiode 111a-UR, the B-color filters 112a-UR and the on-chip lens 113a-UR are disposed in order from the bottom.

As described above, in the example in FIG. 4, in the N-divided pixel unit 100a of a configuration of the present technology, as for the color filter disposed over the N photodiodes, two types of color filters such as the A-color filters 112a-UL and 112a-DR and the B-color filters 112a-UR and 112a-DL are employed, and color filters of identical type are disposed on a diagonal line. The color filter employed for the N-divided pixel unit of a configuration of the present technology is not particularly limited to the example in FIG. 4, but two or more kinds of plural color filters may be arbitrary employed.

[Spectral Characteristic of the Output Light]

Figure 5:
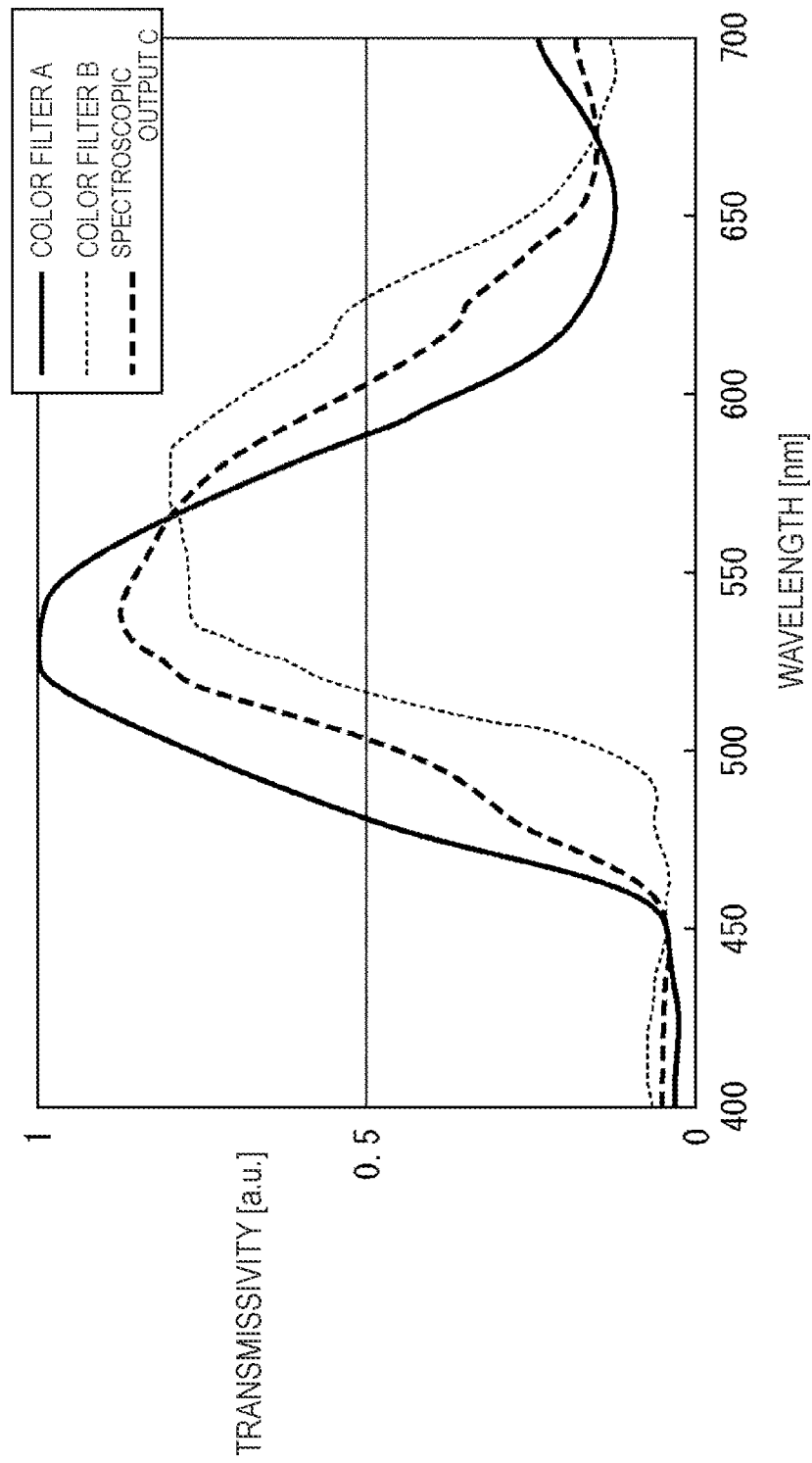
FIG. 5 is a diagram showing spectral characteristics of the lights output from a photodiode.

In the pixel unit of a configuration of the present technology; i.e. in the pixel unit in which plural color filters is disposed in different positions on a plane within one pixel unit, the electrical signal output from the photodiode is a result of combination of spectral characteristics of plural color filters as shown in FIG. 5.

FIG. 5 is a diagram showing spectral characteristics of the light output from the photodiode in the pixel unit of a configuration of the present technology. In FIG. 5, the vertical axis represents the transmissivity; and the horizontal axis represents the wavelength.

The A-color filters 112-UR and 112-DR disposed on the single pixel unit 100 of a configuration of the present technology has a characteristic that the transmissivity is the highest in a range of wavelength 520 to 540 nm as indicated with a solid line. The B-color filters 112-UR and 112-DL disposed on the single pixel unit 100 of a configuration of the present technology has a characteristic that the transmissivity is the highest in a range of wavelength 530 to 580 nm as indicated with a dotted line.

The photodiode 111 disposed on the single pixel unit 100 of a configuration of the present technology receives the light passing through the A-color filters 112-UR and 112-DR and the B-color filters 112-UR and 112-DL which have the above characteristics. In this case, it is the spectral characteristic of the light as the result of combination of the characteristics of the A-color filters 112-UR and 112-DR and the B-color filters 112-UR and 112-DL that enters the photodiode 111; i.e. a characteristic of spectroscopic output C indicated with a dotted line in FIG. 5. Accordingly, in the single pixel unit 100 of a configuration of the present technology, the photodiode 111 outputs an electrical signal of a level corresponding to the spectroscopic output C.

Likewise, the N photodiodes disposed on the N-divided pixel unit 100a of a configuration of the present technology receives the light passing through the A-color filters 112a-UL and 112a-DR and the B-color filters 112a-UR and 112a-DL which has the characteristics shown in FIG. 5. In this case, when every spectral characteristics of the light entering the N photodiodes are combined, a result of combination of characteristics of the A-color filters 112a-UL and 112a-DR and the B-color filters 112a-UR and 112a-DL is obtained; i.e., the characteristic of the spectroscopic output C indicated with a dotted line in FIG. 5 are obtained. Accordingly, in the N-divided pixel unit 100a of a configuration of the present technology, an electrical signal of a level as a sum of every levels corresponding to the amount of light received by the N photodiodes; i.e. an electrical signal of a level corresponding to the spectroscopic output C is output from a common FD section 201 (describe below) or an image signal reading section (for example, the image signal reading section at the downstream (for example, the image signal reading section 533 shown in FIG. 20, which will be described below).

As described above, the single pixel unit 100 and the N-divided pixel unit 100a each of a configuration of the present technology are configured including the A-color filters and the B-color filters which have the characteristics shown in FIG. 5, which are disposed with the ratio of 1:1 at different positions on a plane in one pixel unit. With this, the light focused on the photodiode disposed on the single pixel unit 100 has the characteristic of the spectroscopic output C indicated with the dotted line in FIG. 5. When every spectral characteristics of the light entering the N photodiodes of the N-divided pixel unit 100a are combined, the characteristic of the spectroscopic output C indicated with the dotted line in FIG. 5 is obtained. That is, with the single pixel unit 100 the N-divided pixel unit 100a which have the configuration of the present technology, a new spectral characteristic (i.e., the characteristic of the spectroscopic output C) can be created different from the original spectral characteristics caused through the materials for the A-color filter and the B-color filter. That is, a new spectral characteristic can be created without depending on the development of a material for a new color filter.

However, for example, when plural color filters disposed and laminated on an identical position on a plane in one pixel unit, the spectral characteristic of the light output from the photodiode is a result of integration of spectral characteristics of the plural color filters laminated at the identical position on a plane. A detailed description on this point will be made referring to FIG. 6 and FIG. 7.

[Plural Color Filters Disposed at an Identical Position on a Plane within the Pixel Unit]

Figure 6:
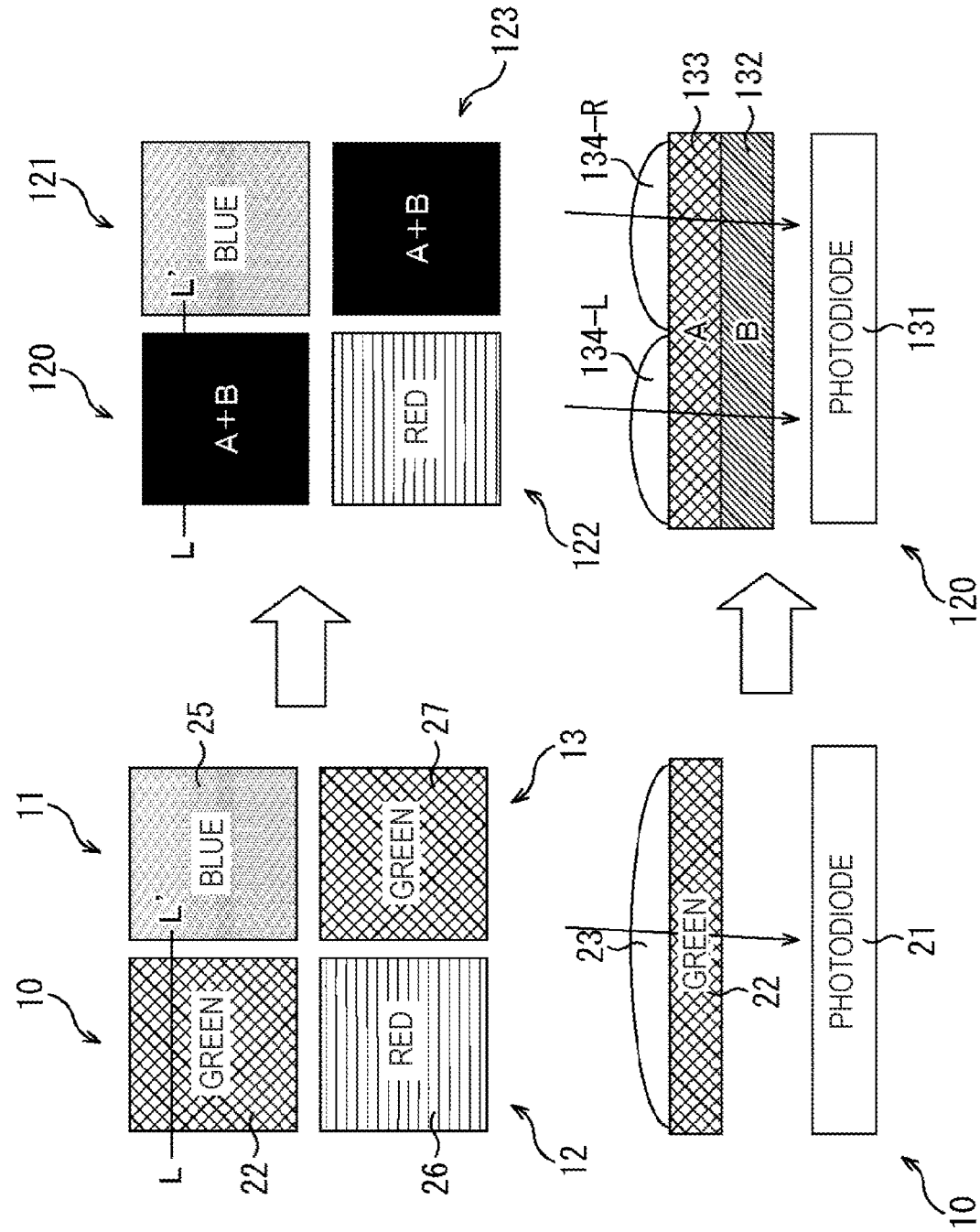
FIG. 6 illustrates an example of a configuration of a single pixel unit including plural color filters disposed and laminated on an identical position on a plane.

FIG. 6 illustrates an example of a configuration of a single pixel unit including plural color filters disposed and laminated on an identical position on a plane.

The single pixel unit 10 of a general configuration is shown at the left side in FIG. 6. Since the description of the single pixel unit 10 of a general configuration has been made referring to FIG. 1A etc, the description thereof is omitted here.

With respect to the single pixel unit 10 of a general configuration, a single pixel unit 120 including plural color filters disposed and laminated on an identical position on a plane is shown at the right side in FIG. 6.

In particular, the figure at the upper-right side in FIG. 6 is a top view of a group of a single pixel unit including single pixel units 120 and 123 in which plural color filters are disposed and laminated on an identical position on a plane. The figure at the lower-right side in FIG. 6 is a cross-sectional view of the single pixel unit 120 taken along a line L-L'.

As shown in the figures at the upper-right side and at the lower-right in FIG. 6, the single pixel unit 120 is configured including, with respect to the single photodiode 131, a B-color filter 132, an A-color filter 133 and a pair of an on-chip lens 134-L and an on-chip lens 134-R being laminated in this order from the bottom. That is, at the identical position on a plane disposed with the photodiode 131, the B-color filter 132 and the A-color filter 133 are disposed and laminated.

[Spectral Characteristic of the Output Light]

Figure 7:
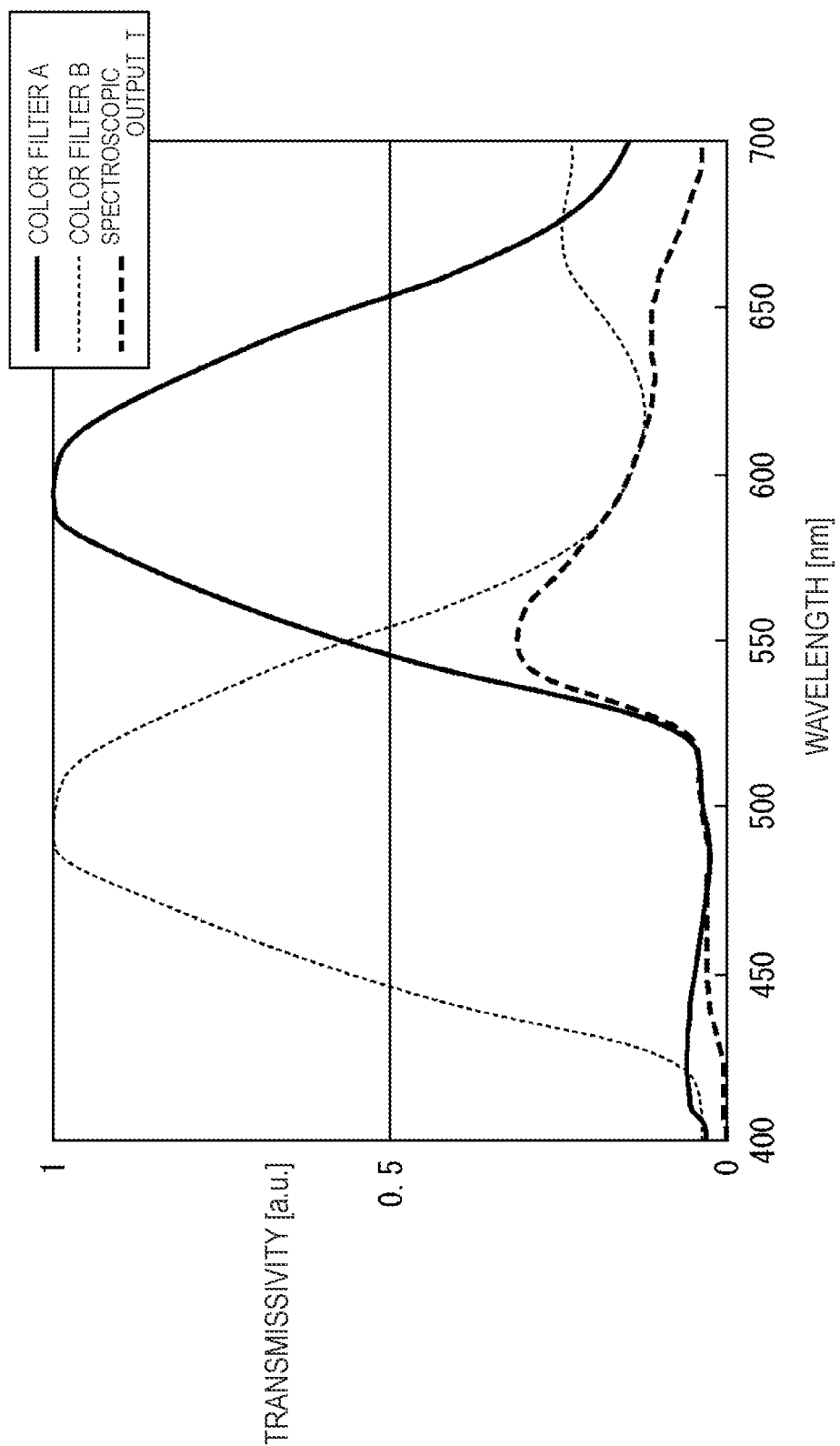
FIG. 7 illustrates spectral characteristics of the lights output from the photodiode in the single pixel unit including plural color filters disposed and laminated on an identical position on a plane.

FIG. 7 illustrates spectral characteristics of the light output from the photodiode 131 in the single pixel unit 120 including plural color filters disposed and laminated on an identical position on a plane as described above. In FIG. 7, the vertical axis represents the transmissivity; and the horizontal axis represents the wavelength.

The A-color filter 133 disposed on the single pixel unit 120 has a characteristic in which the transmissivity is the highest around 600 nm of wavelength as indicated with a solid line in FIG. 7. The B-color filter 132 disposed on the single pixel unit 120 has a characteristic in which the transmissivity is the highest around 500 nm of wavelength as indicated with a dotted line. The photodiode 131 disposed on the single pixel unit 120 receives the light passing through the two color filters of the A-color filter 133 and the B-color filter 132 each having the above characteristic.

In this case, the light entering the photodiode 131 is a result of integration of the characteristic of the B-color filter 132 and the characteristic of the A-color filter 133; i.e., the characteristic of spectroscopic output T indicated with a dotted line in FIG. 7. The reason of this is that, when plural color filters are disposed at an identical position on a plan in the single pixel unit 120, a spectral absorption occurs in each of the plural color filters. Therefore, only the electrical signal of a level corresponding to the result of integration of the spectral characteristics of all color filters positioned at the identical position on a plane in the single pixel unit 120 is output from the photodiode 131.

[Spectral Characteristic of the Light Output from the Pixel Unit Having a Configuration of the Present Technology]

Figure 8:
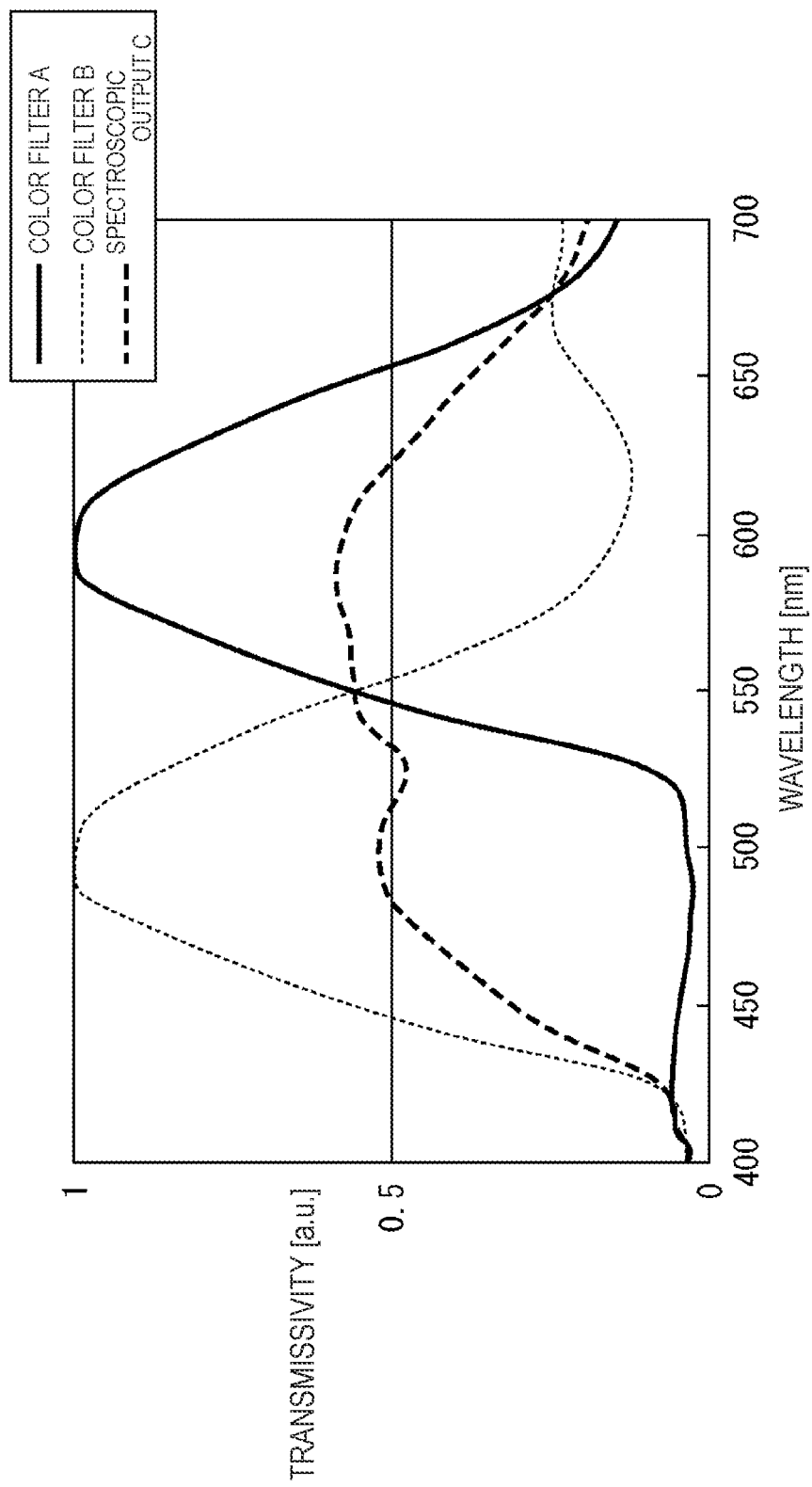
FIG. 8 is a diagram showing the spectral characteristics of the lights, which are output from the photodiode in the pixel unit of a configuration of the present technology.

Contrarily, when the A-color filter and the B-color filter shown in FIG. 7 are used, in the pixel unit of a configuration of the present technology, the spectral characteristic of the light output from the photodiode is as shown in FIG. 8.

FIG. 8 is a diagram showing the spectral characteristic of the light output from the photodiode in the pixel unit of a configuration of the present technology. In FIG. 8, the vertical axis represents the transmissivity; and the horizontal axis represents the wavelength.

As shown in FIG. 8, the A-color filter and the B-color filter disposed on the pixel unit of a configuration of the present technology have the same characteristics as those of the A-color filter 133 and the B-color filter 132 disposed on the single pixel unit 120 which has been described referring to FIG. 7.

The light that enters the photodiode 111 disposed in the single pixel unit 100 of a configuration of the present technology is the light that passes through each of the A-color filters 112-UR and 112-DR and the B-color filters 112-UR and 112-DL, each having the characteristic as described above. In this case, the spectral characteristic of the light that enters the photodiode 111 is a composition result of the characteristics of the A-color filters 112-UR and 112-DR and the B-color filters 112-UR and 112-DL; i.e., the characteristic of the spectroscopic output C indicated with a dotted line in FIG. 8. Accordingly, in the single pixel unit 100 of a configuration of the present technology, the photodiode 111 outputs an electrical signal of a level corresponding to the spectroscopic output C.

Likewise, the light that enters the N photodiodes disposed in the N-divided pixel unit 100a of a configuration of the present technology is the light that passes through the A-color filters 112a-UL and 112a-DR and the B-color filters 112a-UR and 112a-DL, each having the characteristic shown in FIG. 8. In this case, the composition result of the spectral characteristics of the light that enters the N photodiodes is the composition result of the characteristics of the A-color filters 112a-UL and 112a-DR and the B-color filters 112a-UR and 112a-DL; i.e., the characteristic of the spectroscopic output C indicated with a dotted line in FIG. 8. Accordingly, in the N-divided pixel unit 100a of a configuration of the present technology, an electrical signal that has a level in which all levels corresponding to the amount of light received by each of the N photodiodes. That is, an electrical signal of a level corresponding to the spectroscopic output C is output from a common FD section 201 (described below) or the image signal reading section at the downstream (for example, the image signal reading section 533 shown in FIG. 20, which will be described below).

As described above referring to FIG. 3 to FIG. 8, in the single pixel unit 100 and the N-divided pixel unit 100a which have the configuration of the present technology, plural color filters are disposed at different positions on a plane in one pixel unit. Accordingly, a new spectral characteristic can be created without depending on the development of a material for a new color filter.

Here, defining that a unit that receives the light passing through one color filter is a pixel, when plural color filters are disposed at different positions on a plane of one pixel unit, one pixel is included in each of the plural color filters. That is, plural pixels are included in one pixel unit. In order to distinguish the plural pixels included in one pixel unit from a general pixel, the same will be hereinafter referred to as small pixels.

[Dispassion of the On-Chip Lens]

As described referring to FIG. 3 and FIG. 4, in the single pixel unit 100 and the N-divided pixel unit 100a which have the configuration of the present technology, the on-chip lens is disposed for each of the plural color filters disposed at the different positions on a plane in one pixel unit; i.e., the on-chip lens is disposed for each small pixel.

Figure 9:
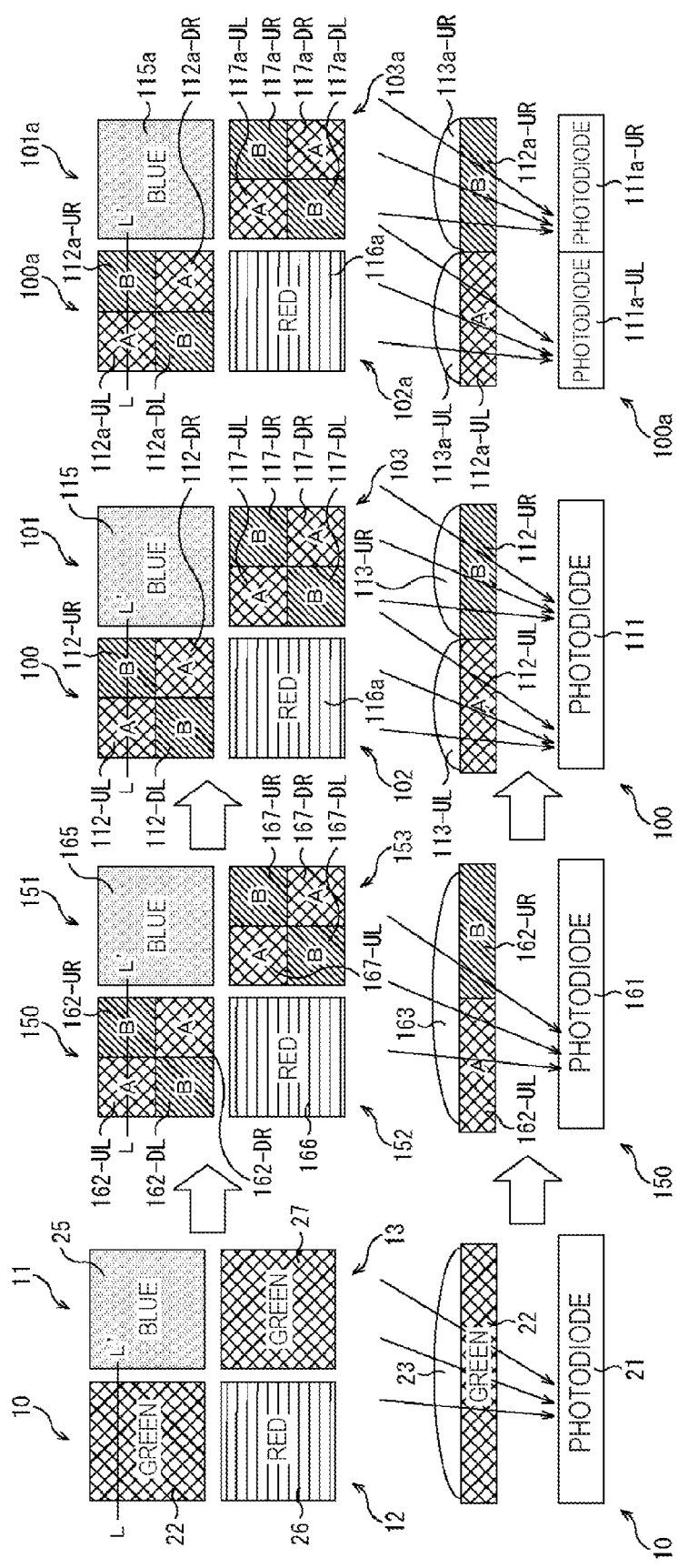
FIG. 9 illustrates the disposition of an on-chip lens.

FIG. 9 illustrates a disposition of the on-chip lenses.

A figure at left end in FIG. 9 illustrates a single pixel unit 10 of a general configuration. Since the description on the single pixel unit 10 of a general configuration has been given referring to FIG. 1A etc, the description thereof is omitted here.

The second figure from the left in FIG. 9 is a top view of a group of the single pixel units 150 and 153, which include plural color filters disposed at different positions on a plane in one pixel unit, and the single pixel units 151 and 152 of a general configuration. The bottom figure is a cross-sectional view of the single pixel unit 150 taken along line L-L'. The single pixel unit 150 is configured including, with respect to a single photodiode 161, a pair of an A-color filter 162-UL and a B-color filter 162-UR and a single on-chip lens 163 being laminated in this order from the bottom.

As shown in the second figure in FIG. 9, in the single pixel unit 150, with respect to the single photodiode 161, although plural color filters are disposed, only one on-chip lens 163 is disposed. In this case, when the light enters the on-chip lens 163 from an oblique direction, the amount of the light passing through the plural color filters is not uniform. Accompanying this, the spectral characteristic of the light entering the photodiode 161 also varies. That is, the spectral characteristic of the light entering the photodiode 161 varies depending on the entering angle of the light which enters the on-chip lens 163. For example, as shown in the example of the second figure from the left in FIG. 9, the amount of the light passing through the B-color filter 162-UR is larger than the amount of the light passing through the A-color filter 162-UL. Thus, the spectral characteristic of the light entering the photodiode 161 varies.

Therefore, as shown in the third and fourth figures from the left in FIG. 9, in the single pixel unit 100 and the N-divided pixel unit 100a which have the configuration of the present technology, the on-chip lens is disposed for the plural color filters disposed at different positions on a plane in one pixel unit; i.e., disposed for each small pixel.

In the single pixel unit 100 of a configuration of the present technology, the on-chip lens 113-UL is dispose on the A-color filter 112-UL; and the on-chip lens 113-UR is disposed on the B-color filter 112-UR. With this, unevenness of the amount of the light passing through the A-color filter 112-UL and the B-color filter 112-UR is reduced, and thus variation of the spectral characteristic of the light entering the photodiode 111 is reduced.

Likewise, in the N-divided pixel unit 100a of a configuration of the present technology also, the on-chip lens 113a-UL is disposed on the A-color filters 112a-UL; and the on-chip lens 113a-UR is disposed on the B-color filters 112a-UR. With this, unevenness of the amount of the light passing through the A-color filters 112a-UL and the B-color filters 112a-UR is reduced, and thus variation of spectral characteristic of the light entering the photodiode 111a-UL and the photodiode 111a-UR is reduced.

By disposing plural color filters and plural on-chip lens at different positions on a plane in one pixel unit as described above, the light focused on the photodiode disposed in each pixel unit is optically combined. With this, the spectral characteristic of the light focused on each photodiode can be controlled to be optimally suitable for the purpose of application.

[Example of a Configuration of Single Pixel Unit of a Configuration of the Present Technology Formed with a Waveguide]

In the photodiode disposed in one pixel unit may not ensure a uniform photoelectric conversion due to non-uniformity of ion implantation or the like. Unevenness may be generated in the sensitivity of the photodiode.

Figure 10:
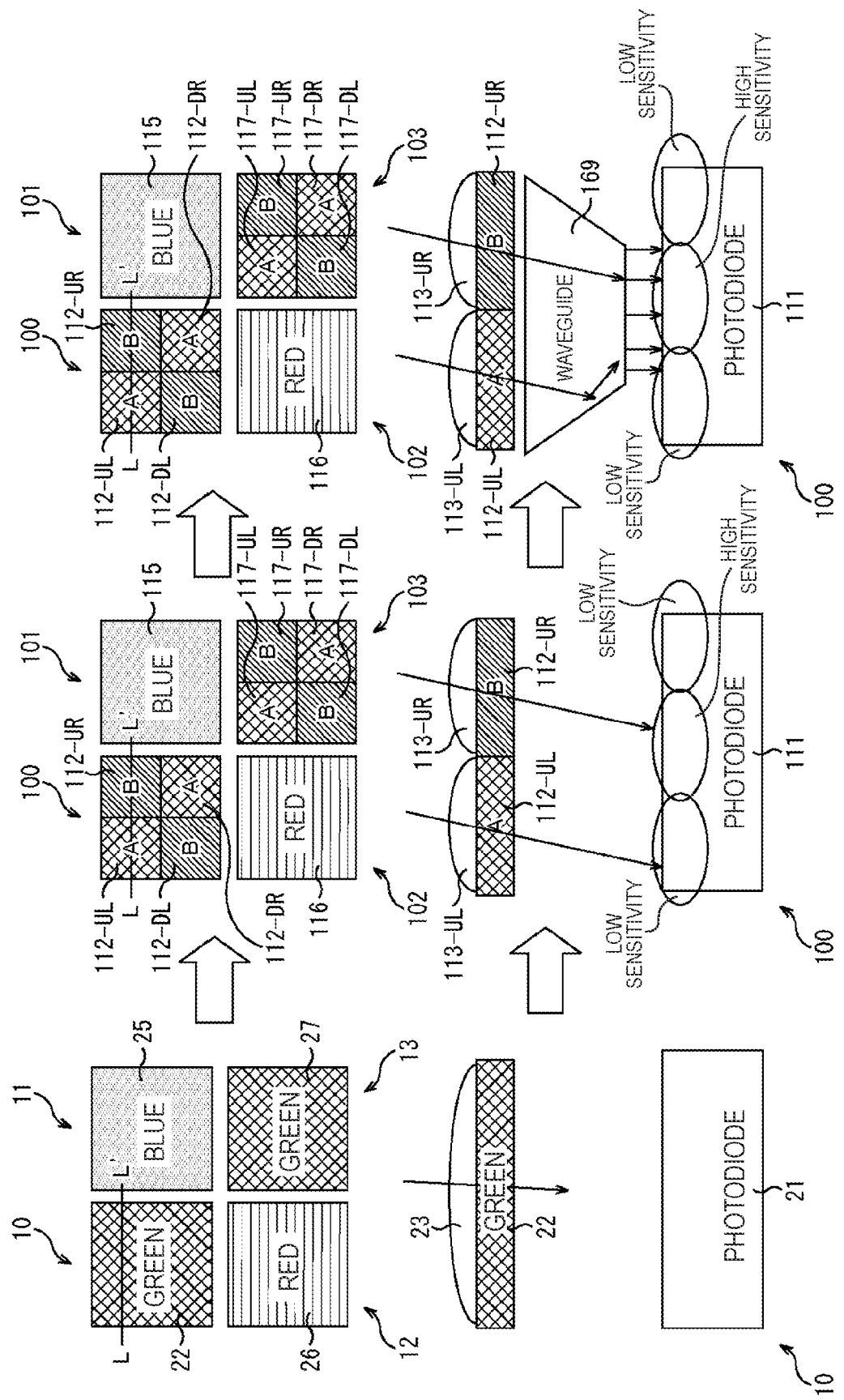
FIG. 10 illustrates an example of a configuration of a single pixel unit of a configuration of the present technology which is formed with a waveguide.

FIG. 10 illustrates an example of a configuration of a single pixel unit of a configuration of the present technology formed with a waveguide.

The single pixel unit 10 of a general configuration is shown at the left side in FIG. 10. The description of the single pixel unit 10 of a general configuration has been made referring to FIG. 1A etc. The description thereof is omitted here.

In the center of FIG. 10, the single pixel unit 100 of a configuration of the present technology is shown. The description of the single pixel unit 100 of a configuration of the present technology has been made referring to the figure at the right side in FIG. 3. The description thereof is omitted here.

It is assumed that the photodiode 111 has unevenness in the sensitivity such that, for example, the edge area of the acceptance surface has a low sensitivity; and the central area thereof has a high sensitivity as shown in the center-bottom figure in FIG. 10. In this case, for example, even when the light intensity is the same between the light which passes through the A-color filter 112-UL and enters the edge area of the photodiode 111 and the light which passes through the B-color filter 112-UR and enters the central area of the photodiode 111, the light intensity in the central area is higher that that in the edge area; and an electrical signal of higher level is output in the central area.

Therefore, when unevenness is found in the sensitivity of the photodiode 111 as shown in the center low figure in FIG. 10, for example, a waveguide 169 is disposed over the photodiode 111 as shown in the figure at the lower-right in FIG. 10. With this, the light passing through the A-color filter 112-UL and the light passing through the B-color filter 112-UR is once collected by the waveguide 169 and is allowed to enter the central area of the photodiode 111 having higher sensitivity. Therefore, when the light intensity is the same between the light passing through the A-color filter 112-UL and the light passing through the B-color filter 112-UR, output electrical signals have the same level.

By disposing the waveguide 169 in the single pixel unit 100 of a configuration of the present technology as described above, the light focused on the photodiode 111 is optically combined while reducing the influence by the unevenness of the sensitivity in the photodiode 111. With this, the spectral characteristic of the light focused on each photodiode can be controlled optimally to be suitable for the purpose of application.

As described above, with the pixel unit of a configuration of the present technology, the spectral characteristic of the light focused on the photodiode can be controlled by optically combining the light. A description will be made below while giving an example to control the spectral characteristic of the light focused on the photodiode by electrically combining the light.

[N-Divided Pixel Unit to which First Adding Technique is Applied]

In the N-divided pixel unit, an electrical signal having a level, in which every levels each corresponding to the amount of received light of the N photodiodes are added, is output. As described above, as for the technique to add each of the electrical signals of the N photodiodes, a first technique and a second technique area available.

Figure 11:
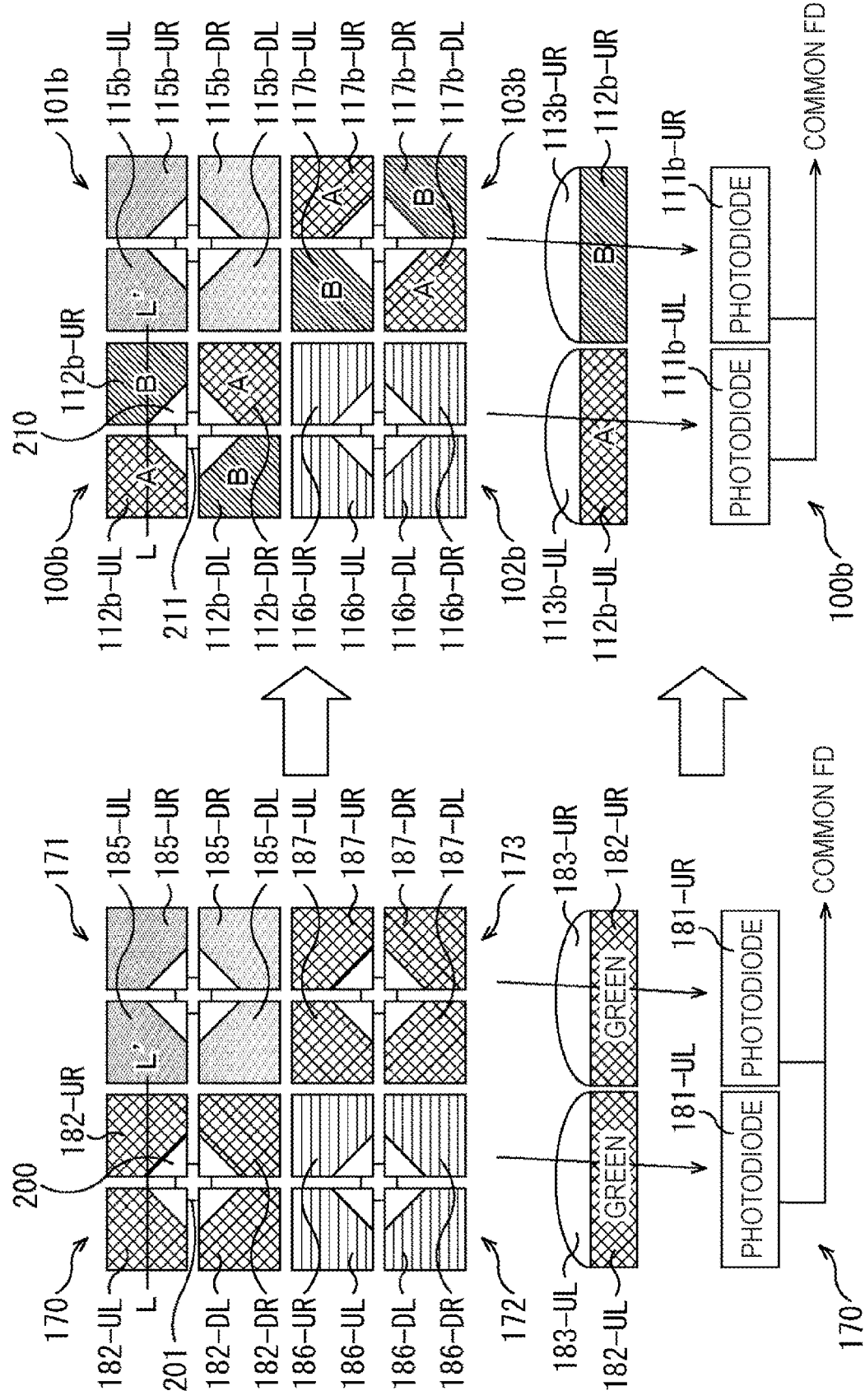
FIG. 11 illustrates an example of a configuration of an N-divided pixel unit to which the first adding technique is applied.

FIG. 11 illustrates an example of a configuration of an N-divided pixel unit to which the first adding technique is applied.

An N-divided pixel unit 170 of a general configuration, to which the first adding technique is applied, is shown at the left side in FIG. 11. An N-divided pixel unit of a configuration of the present technology 100b, to which the first adding technique is applied, is shown at the right side in FIG. 11.

The figure at the upper-left in FIG. 11 is a top view of a group of neighboring four N-divided pixel units 170 to 173 of a general configuration to which the first adding technique is applied.

The N-divided pixel unit 170 is disposed with four green color filters 182-UL, 182-UR, 182-DL and 182-DR. Each of the four green color filters is disposed with a transfer gate 200 indicated with a triangle. And at the central portion of the four green color filters, a common FD section 201 is disposed.

The N-divided pixel unit 171 is disposed with four blue color filters 185-UL, 185-UR, 185-DL and 185-DR. Each of the four green color filters is disposed with a transfer gate 200. And at the central portion of the four green color filters, a common FD section 201 is disposed.

The N-divided pixel unit 172 is disposed with four red color filters 186-UL, 186-UR, 186-DL and 186-DR. Each of the four green color filters is disposed with a transfer gate 200. And at the central portion of the four green color filters, a common FD section 201 is disposed.

The N-divided pixel unit 172 is disposed with four green color filters 187-UL, 187-UR, 187-DL and 187-DR. Each of the four green color filters is disposed with a transfer gate 200. And at the central portion of the four green color filters, a common FD section 201 is disposed.

As shown in the figure at the lower-left in FIG. 11, in accordance with the first adding technique, electrical signals of a level corresponding to the amount of the lights, which are received by the four green photodiodes 181-UL, 181-UR, 181-DL and 181-DR of the N-divided pixel unit 170, are transferred to the transfer gate 200, and then to the common FD section 201 respectively. The common FD section 201 outputs a signal equivalent to every electrical signals added; i.e., an electrical signal having a level equivalent to every levels summed. The common FD section 201 simultaneously reads every charge accumulated to thereby add the electrical signals of a level corresponding to the read charge. Thus, according the first adding technique, the every electrical signals of various levels from each of the N (in this case, 4) photodiodes are added; and the N-divided pixel unit 170 outputs an electrical signal of a level after the summation.

Likewise, in the N-divided pixel units 171 to 173 also, electrical signals of a level corresponding to the amount of the light received by the respective photodiodes are transferred to each transfer gate 200; and each signal is transferred to the common FD section 201. Each of the N-divided pixel units 171 to 173 outputs an electrical signal of a level after summation of every electrical signals made by the common FD section 201.

The figure at the upper-right in FIG. 11 is a top view of a group of the N-divided pixel units 100b and 103b of a configuration of the present technology and the N-divided pixel units 101b and 102b of a general configuration to which the first adding technique is applied.

The N-divided pixel unit 100b of a configuration of the present technology is disposed with the A-color filters 112b-UL and 112b-DR and the B-color filters 112b-UR and 112b-DL. Each of the four color filters is disposed with a transfer gate 210 indicated with a triangle. Further in the central portion of the four color filters, a common FD section 211 is disposed.

The N-divided pixel unit 101b of a general configuration is disposed with four blue color filters 115b-UL, 115b-UR, 115b-DL and 115b-DR. Each of the four color filters is provided with the transfer gate 210. Further, in the central portion of the four color filters, the common FD section 211 is disposed.

The N-divided pixel unit 102b of a general configuration is disposed with red color filters 116b-UL, 116b-UR, 116b-DL and 116b-DR. Each of the four color filters is provided with the transfer gate 210. Further, in the central portion of the four color filters, the common FD section 211 is disposed.

The N-divided pixel unit 103b of a configuration of the present technology is disposed with the B-color filters 117b-UL and 117b-DR and the A-color filter 117b-UR and 117b-DL. Each of the four color filters is provided with the transfer gate 210. Further, in the central portion of the four color filters, the common FD section 211 is disposed.

As shown in the figure at the lower-right in FIG. 11, in accordance with the first adding technique, the electrical signals of a level corresponding to the amount of the light received by the A-photodiodes 111b-UL and 111b-DR and B-photodiodes 111b-UR and 111b-DL of the N-divided pixel unit 100b of a configuration of the present technology are transferred to each transfer gate 210, and then to the common FD section 211 respectively. The N-divided pixel unit 100b outputs a signal equivalent to every electrical signals added; i.e., an electrical signal of a level equivalent to the sum of the signals of various levels are summed by the common FD section 211. The common FD section 211 simultaneously reads every charge accumulated to thereby add electrical signals of a level equivalent to the read charge.

Likewise, in the N-divided pixel units 101b to 103b also, electrical signals of various levels corresponding to the amount of the light received by the respective photodiodes are transferred to each transfer gate 210, and then transferred to the common FD section 211.

In this case, the spectral characteristic of the light output from the N-divided pixel units 100b and 103b of a configuration of the present technology has a characteristic of the spectroscopic output C indicated with the dotted line in FIG. 5. That is, the N-divided pixel units 100b and 103b outputs an electrical signal of a level corresponding to the composition result of the spectral characteristics of the plural color filters disposed at the different positions on a plane in the N-divided pixel units 100b and 103b. That is, with the N-divided pixel units 100b and 103b of a configuration of the present technology, a new spectral characteristic, which is different from the original spectral characteristics obtained by the material for the A-color filter and the B-color filter, can be created.

[Adjustment of Spectral Characteristic using a Gain]

In the N-divided pixel units 100b and 103b of a configuration of the present technology shown at the right side in FIG. 11, the common FD section 211 simultaneously reads the electrical signals of the plural photodiodes each having different level corresponding to the amount of received light and simply adds the electrical signals. However, the common FD section 211 may read electrical signals at different timing for each of the photodiodes which receives the light having identical spectral characteristic, and add the electrical signals the level of which being amplified with an individually preset gain.

Figure 12:
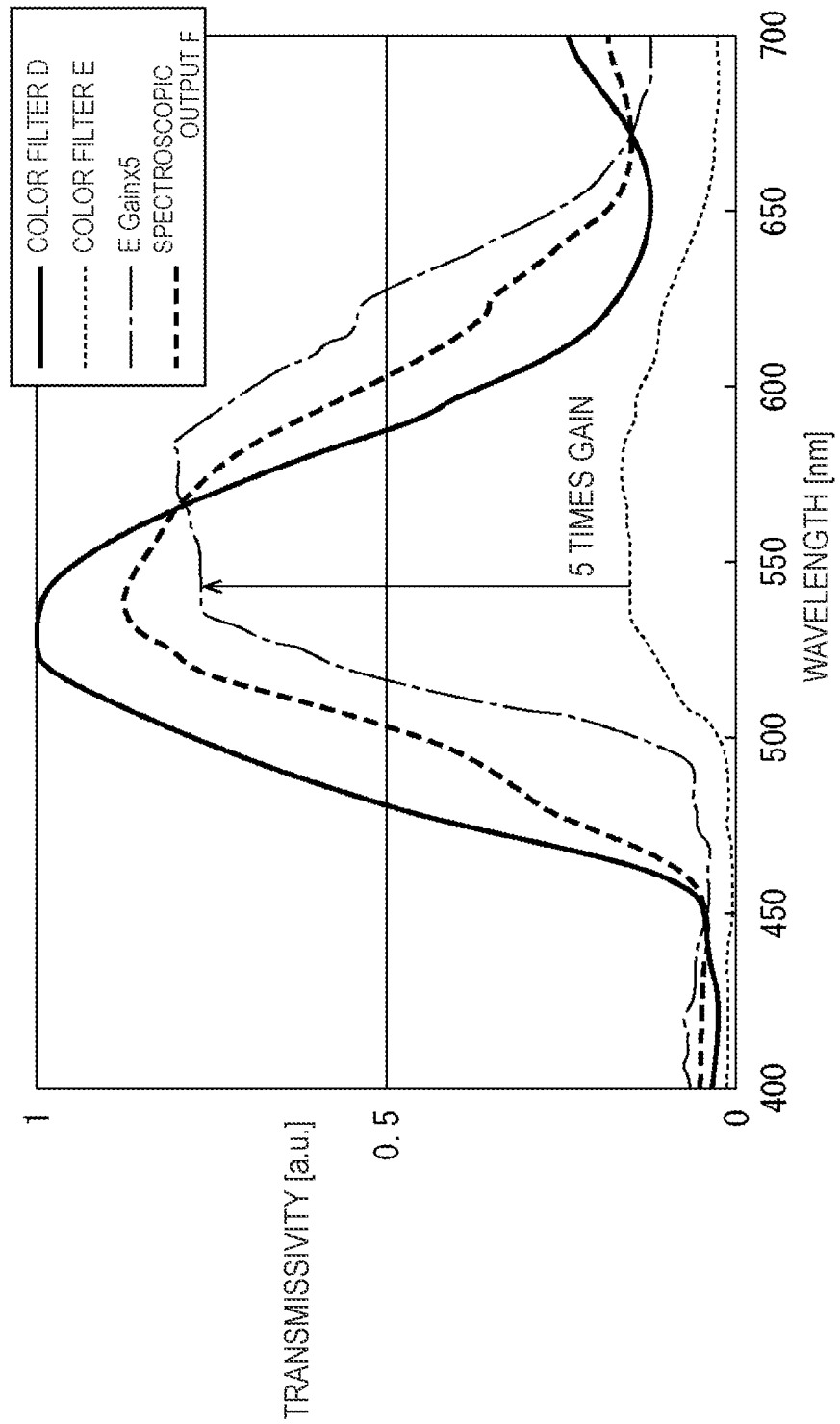
FIG. 12 is a diagram showing spectral characteristics of the lights output from the photodiode.

Here, it is assumed that, in the N-divided pixel units 100b and 103b of a configuration of the present technology shown at the right side in FIG. 11, the A-color filters and the B-color filters, which are disposed with a number of 1:1 ratio, are replaced with, for example, D-color filters and E-color filters respectively, each having a characteristic shown in FIG. 12.

FIG. 12 shows the spectral characteristics of the lights output from the photodiodes in the N-divided pixel units 100b and 103b of a configuration of the present technology which are disposed with the D-color filters and E-color filters with a number 1:1 ratio. In FIG. 12, the vertical axis represents the transmissivity; and the horizontal axis represents the wavelength.

The D-color filter disposed in the N-divided pixel units 100b and 103b of a configuration of the present technology has a characteristic such that the transmissivity is highest in a range of 520 to 540 nm of wavelength as indicated with a solid line in FIG. 12. Also, the E-color filter disposed in the N-divided pixel units 100b and 103b of a configuration of the present technology has a characteristic such that the transmissivity is highest in a range of 540 to 590 nm of wavelength as indicated with a solid line in FIG. 12.

In this case, the common FD section 211 disposed in the N-divided pixel units 100b and 103b of a configuration of the present technology may read, at different timing, electrical signals of a level corresponding to the spectral characteristic of the D-color filter and the E-color filter and directly add these electrical signals. With this, electrical signals of the same number as the color filter types; i.e., in this case, two different electrical signals can be obtained.

The common FD section 211 may also read electrical signals at different timing for each photodiode which receives the light having an identical spectral characteristic, and then add the electrical signals of a level amplified by an individually preset gain. The gain is set by the image signal reading section at the downstream (for example, the image signal reading section 533 shown in FIG. 20, which will be described below).

For example, when the gain of the electrical signal of a level corresponding to the amount of received light which passes through the E-color filter and enters the photodiode is set to 5 times, the transmissivity has a characteristic such that the spectroscopic output F is amplified by 5 times in range of 540 to 590 nm of wavelength as indicated with a chain line in FIG. 12.

Therefore, in the N-divided pixel units 100b and 103b of a configuration of the present technology, a composition result of the spectral characteristic of the color filter D and the spectral characteristic in which the gain of the color filter E is amplified by 5 times; i.e., an electrical signal of a level which corresponds to the characteristic of the spectroscopic output F indicated with a dotted line in FIG. 12 is output. As described above, after reading electrical signals at different timing for each photodiode which receives the light of identical spectral characteristic, the electrical signals, the level of which is amplified by an individually preset gain, are added; thereby a new spectral characteristic can be created. Thus, by electrically combining the spectral characteristics of plural color filters, the spectral characteristic can be optimally controlled to be suitable for the purpose of application.

[N-Divided Pixel Unit to which Second Adding Technique is Applied]

Subsequently, a description will be made on an N-divided pixel unit to which a second adding technique is applied.

Figure 13:
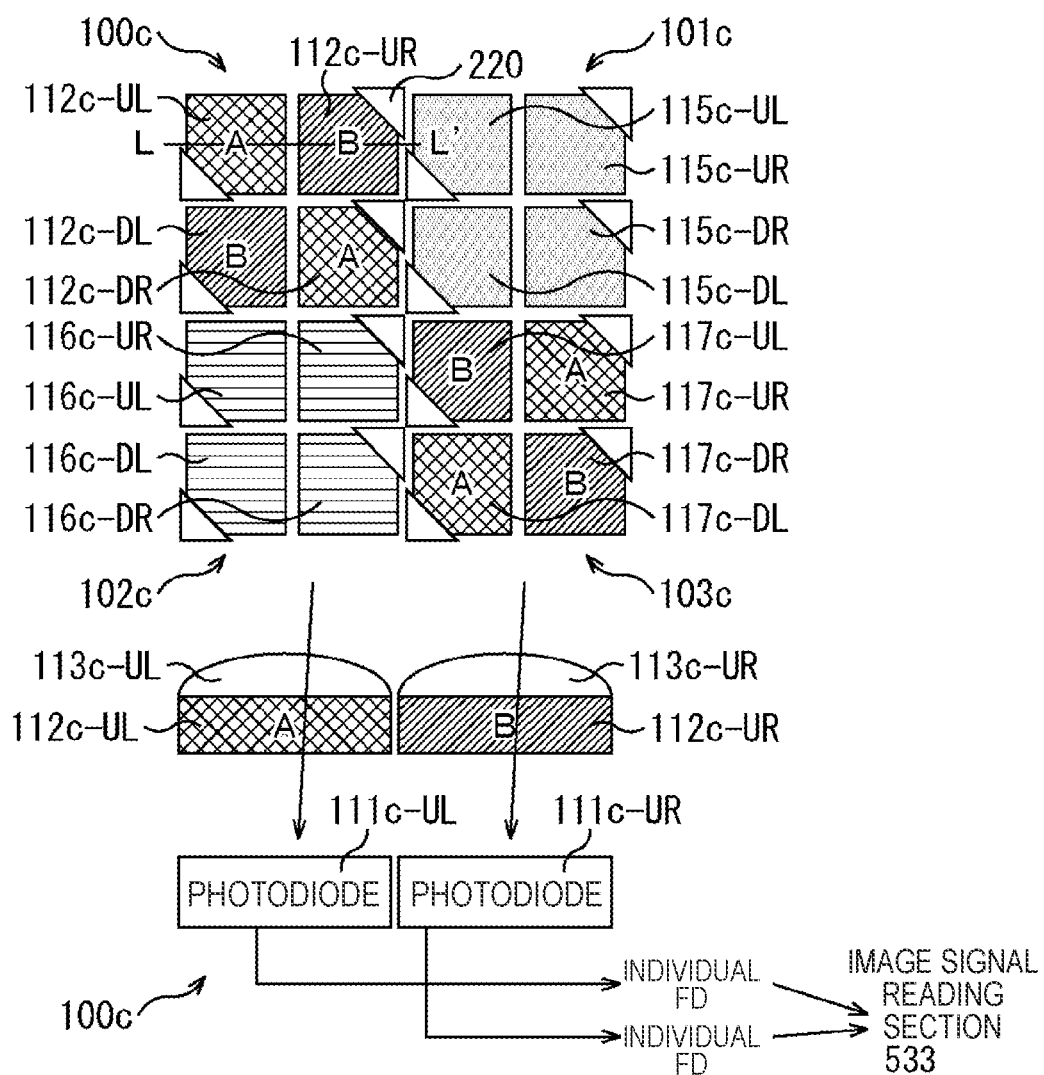
FIG. 13 illustrates an example of a configuration of an N-divided pixel unit to which a second adding technique is applied.

FIG. 13 illustrates an example of a configuration of the N-divided pixel unit to which the second adding technique is applied.

The upper figure in FIG. 13 is a top view of a group of N-divided pixel units 100c and 103c of a configuration of the present technology, to which the second adding technique is applied, and N-divided pixel units 101c and 102c of a general configuration.

In the N-divided pixel unit 100c of a configuration of the present technology, A-color filters 112c-UL and 112c-DR and B-color filters 112c-UR and 112c-DL are disposed. Also, each of the four color filters is provided with a transfer gate, which is indicated with a triangle, and an individual FD section 220. That is, the transfer gate and the individual FD section 220 are laminated at the same position.

In the N-divided pixel unit 101c of a general configuration, four blue color filters 115c-UL, 115c-UR, 115c-DL and 115c-DR are disposed. Also, each of the four color filters is provided with a transfer gate and an individual FD section 220.

In the N-divided pixel unit 102c of a general configuration, four red color filters 116c-UL, 116c-UR, 116c-DL and 116c-DR are disposed. Also, each of the four color filters is provided with a transfer gate and an individual FD section 220.

In the N-divided pixel unit 103c of a configuration of the present technology, B-color filters 117c-UL and 117c-DR and A-color filters 117c-UR and 117c-DL are disposed. Also, each of the four color filters is provided with a transfer gate and an individual FD section 220.

According to the second adding technique, the electrical signals of a different level corresponding to the amount of received light at each of the A-photodiodes 111c-UL and 111c-DR and B-photodiodes 111c-UR and 111c-DL in the N-divided pixel unit 100c of a configuration of the present technology are transferred to the transfer gate and the individual FD section 220 respectively as shown in the bottom figure in FIG. 13. Every electrical signals are separately output from each of the transfer gate and the individual FD sections 220, and are added by the image signal reading section at the downstream (for example, the image signal reading section 533 shown in FIG. 20, which will be described below).

Likewise, in the N-divided pixel units 101c to 103c also, the electrical signals each having a different level corresponding to the amount of received light at the respective photodiodes are transferred to the transfer gate and the individual FD section 220 respectively, and then added by the image signal reading section at the downstream (for example, the image signal reading section 533 shown in FIG. 20, which will be described below).

In this case, the spectral characteristic of the light output from the N-divided pixel units 100c and 103c of a configuration of the present technology has a characteristic indicated with a dotted line in FIG. 5. That is, an electrical signal of a level, which corresponds to the composition result of the spectral characteristics of plural color filters disposed at different positions on a plane in the N-divided pixel units 100c and 103c, is output from the N-divided pixel units 100c and 103c. That is, with the N-divided pixel units 100c and 103c of a configuration of the present technology, a new spectral characteristic, which is different from the spectral characteristics of the original materials for the A-color filter and the B-color filter, can be created.

Same as the N-divided pixel units 100c and 103c of a configuration of the present technology to which the first adding technique is applied, it is assumed that, in the N-divided pixel units 100c and 103c of a configuration of the present technology to which the second adding technique is applied, the filters are replaced with, for example, a D-color filter and an E-color filter each having a characteristic shown in FIG. 12.

In this case also, in the N-divided pixel units 100c and 103c of a configuration of the present technology to which the second adding technique is applied, the electrical signals each having a level corresponding to the spectral characteristic of the D-color filter or the E-color filter may be read at different or same timing, and then added by unshown image signal reading section. With this, electrical signals of the same number as the types of the color filters; i.e., in this case, two different electrical signals can be obtained.

The image signal reading section at the downstream (for example, the image signal reading section 533 shown in FIG. 20, which will be described below) may be configure as below. That is, before adding the electrical signals each having a different level, plural gains different from each other are set for the lights each having an identical spectral characteristic; and after reading the electrical signals at different or same timing, the electrical signals each having a level amplified by the respective gains are added. With this also, a new spectral characteristic can be created by the N-divided pixel units 100c and 103c of a configuration of the present technology to which the second adding technique is applied. By electrically combining the spectral characteristics of plural color filters as described above, the spectral characteristics can be optimally controlled to be suitable for the purpose of application.

In the N-divided pixel unit of a configuration of the present technology which has been described referring to figures at the right side in FIG. 11 and in FIG. 13, the electrical signals from the N photodiodes are output after all of the signals are added; or added after all of the signals are output. However, in the N-divided pixel unit of a configuration of the present technology, each of the electrical signals from the N photodiodes may be separately output without being added, and may be directly used as one electrical signal by the image signal reading section at the downstream (for example, the image processing section 515 shown in FIG. 20, which will be described below).

For example, in the calculation in a linear matrix, the larger number of types of electrical signals corresponding to the colors is available for the calculation, the higher color reproducibility of output image is obtained. Therefore, there is known a technique in which, in order to enhance the color reproducibility, for example, a part of green photodiodes is replaced with emerald photodiodes to thereby increase the types of electrical signals corresponding to the colors available for calculation. However, when a part of the green photodiodes is replaced with emerald photodiodes, the resolution may deteriorate due to reduction of the number of the green photodiodes.

Contrarily to this, in the N-divided pixel unit of a configuration of the present technology, when an emerald photodiode is used, a green photodiode and an emerald photodiode are disposed within a one pixel unit. As a result, both of the number and the resolution of green photodiodes are ensured.

Thus, in the N-divided pixel unit of a configuration of the present technology, each of the electrical signals from the N photodiodes can be used separately for signal processing. Therefore, the number of electrical signals corresponding to the colors available for signal processing can be increased. Accordingly, the color reproducibility can be enhanced while ensuring the resolution.

As described above, in the N-divided pixel unit of a configuration of the present technology, three techniques are available as the techniques for outputting the level of the electrical signal from each of the N photodiodes. In the first technique, levels of the electrical signals from each of the N photodiodes are directly summed, and then an electrical signal of a summed level is output. In the second technique, each level of the electrical signals from each of the N photodiodes is amplified by individually preset gain and summed; and then an electrical signal of a summed level is output. In the third technique, each of the electrical signals from the N photodiodes is separately output. By selectively applying these three output techniques, plural different outputs can be obtained.

Using these techniques, outputs of electrical signals can be controlled to switch among three outputting mode; i.e., transmission timing from the transfer gate and/or individual FD; addition ON/OFF of electrical signals; and the image signal reading section at the downstream (for example, the control section 514 shown in FIG. 20, which will be described below). Therefore, by performing above controls, even the same image sensor, outputs of different spectral characteristics suitable for with the purpose of application (for example, a standard camera, a medical device etc), or circumstances (for example, color temperature, illuminance etc) can be obtained.

[Application of Wide Dynamic Range]

Figure 14:
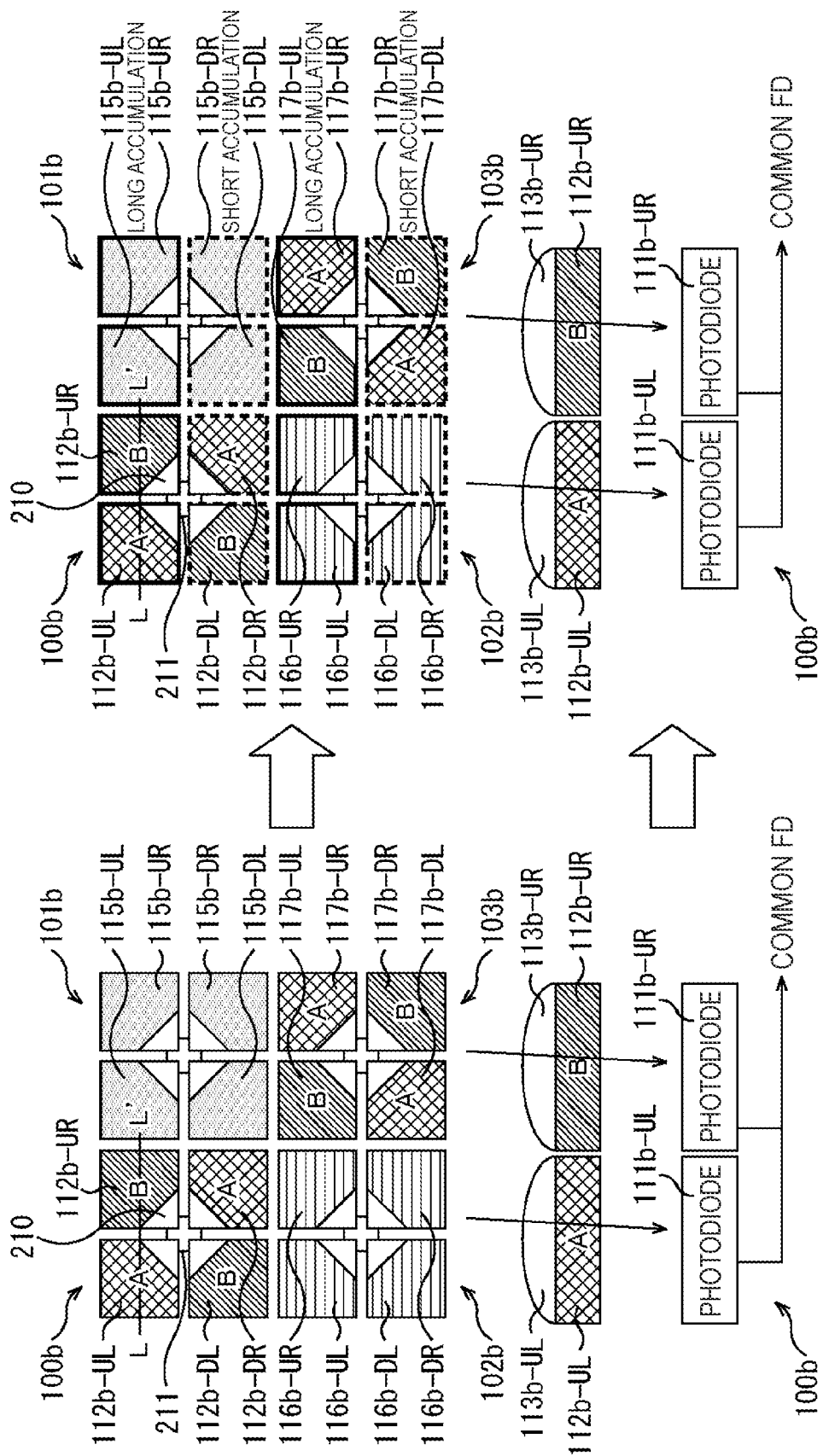
FIG. 14 illustrates an N-divided pixel unit of a configuration of the present technology in which accumulating time for each small pixel is changed.

In the N-divided pixel unit of a configuration of the present technology, by changing the accumulating time of the light (charge) for each small pixel as shown in FIG. 14, the wide dynamic range can be applied.

FIG. 14 illustrates an N-divided pixel unit of a configuration of the present technology in which the accumulating time of charge for each small pixel is changed.

FIG. 14 is a top view of a group of the N-divided pixel units 100b and 103b of a configuration of the present technology and the N-divided pixel units 101b and 102b of a general configuration to which the first adding technique is applied. Since the description of the above has been made while referring to FIG. 11 etc, the description thereof will be omitted here.

In the N-divided pixel units 100b to 103b at the left side in FIG. 14, the accumulating time of charge in the small pixels is the same.

Contrarily, in the N-divided pixel units 100b to 103b at the right side in FIG. 14, the accumulating time of charge for each small pixel is changed.

In particular, the A-color filters 112b-UL and B-color filter 112b-UR disposed in the N-divided pixel unit 100b of a configuration of the present technology are adapted to a long period accumulation (hereinafter, referred to as long accumulation). Contrarily, the A-color filters 112b-DL and the B-color filter 112b-DR disposed in the N-divided pixel unit 100b of a configuration of the present technology are adapted to short period accumulation (hereinafter, referred to as short accumulation).

In the N-divided pixel unit 101b of a general configuration also, the blue color filters 115b-UL and 115b-UR are adapted to long accumulation; the blue color filters 115b-DL and 115b-DR are adapted to short accumulation.

In the N-divided pixel unit 102b of a general configuration also, the blue color filters 116b-UL and 116b-UR are adapted to long accumulation; the blue color filters 116b-DL and 116b-DR are adapted to short accumulation.

The B-color filter 117b-UL and the A-color filter 117b-UR disposed in the N-divided pixel unit 103b of a configuration of the present technology are adapted to long accumulation; the A-color filter 117b-DL and the B-color filter 117b-DR are adapted to short accumulation.

In this case, in the N-divided pixel units 100b to 103b, both of the A-color filter and the B-color filter are disposed in each of the small pixels of long accumulation and each of the small pixels of short accumulation. Therefore, in the N-divided pixel units 100b to 103b, in both of the small pixel of long accumulation and the small pixel of short accumulation, an output which has a new spectral characteristic is obtained as a composition result of the spectral characteristics of the A-color filter and the B-color filter. That is, with the N-divided pixel unit of a configuration of the present technology, an output of a new spectral characteristic can be obtained by applying the wide dynamic range.

[Example Color Filters Disposed in Pixel Unit]

In the above-described example, in a pixel unit of a configuration of the present technology, the green color filter is replaced with plural color filters (i.e., A-color filter and B-color filter). However, other color filter, for example, a red color filter or a blue color filter may be replaced with plural color filters. In the pixel unit of a configuration of the present technology, a color filter of a pigment material or a dye material may be disposed. The pixel unit of a configuration of the present technology is applicable to pixels which are disposed in bayer array, clear bit array, or other array.

In the above example, in the pixel unit of a configuration of the present technology, a green color filter is divided into four, and replaced with plural color filters of a number 1:1 ratio (i.e., two A-color filters and two B-color filters) respectively. However, the number of divisions (i.e. number of small pixels) and the ratio of number of plural color filters are not limited to the above.

In the above example, in the pixel unit of a configuration of the present technology, the A-color filter and the B-color filter are disposed with a ratio of 1:1(i.e., two each). Therefore, the light output from the pixel unit of a configuration of the present technology has a spectral characteristic of an intermediate characteristic between the characteristics of the A-color filter and the B-color filter as a composition result of characteristics of the A-color filter and the B-color filter same as the spectroscopic output C in FIG. 5. Contrarily, when the A-color filter and the B-color filter are disposed with a ratio of 3:1 for example, the light output from the pixel unit of a configuration of the present technology has a characteristic closer to the spectral characteristic of the A-color filter shown in FIG. 5 as a composition result of the characteristics of the A-color filter and the B-color filter.

Figure 15:
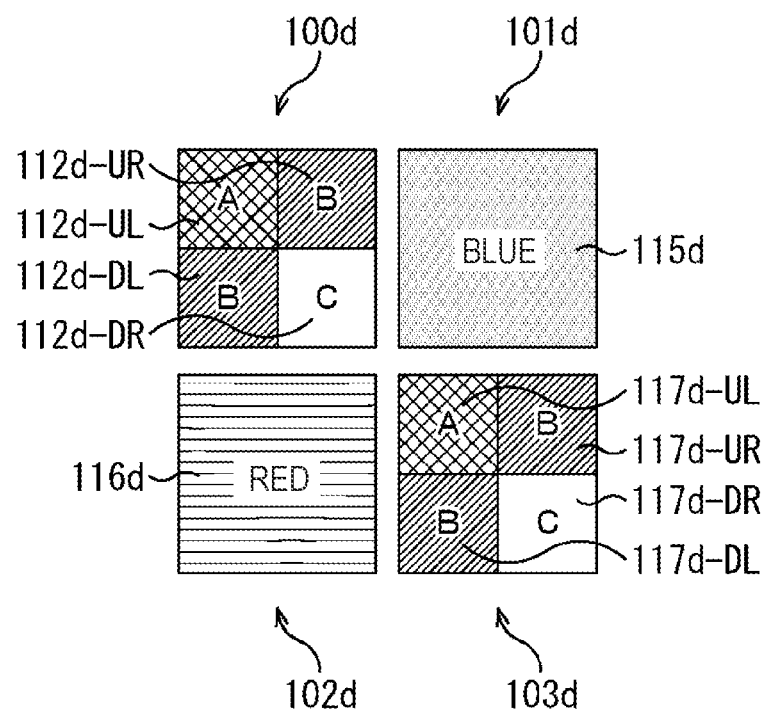
FIG. 15 is a top view of N-divided pixel units of a configuration of the present technology in which three color filters are disposed.

In the pixel unit of a configuration of the present technology, maximum number of the color filters disposable in one pixel unit is equal to the division number of the pixel units; i.e., equal to the number of small pixels. Referring to FIG. 15, a description will be made on the N-divided pixel unit of a configuration of the present technology in which three color filters are disposed.

FIG. 15 is a top view of a group of N-divided pixel units 100d and 103d of a configuration of the present technology in which three color filters are disposed and the N-divided pixel units 101d and 102d of a general configuration.

In the N-divided pixel unit 100d of a configuration of the present technology, an A-color filter 112d-UL, B-color filters 112d-UR and 112d-DL and a C-color filter 112d-DR are disposed. That is, in the N-divided pixel unit 100d of a configuration of the present technology, the A-color filter, the B-color filters and the C-color filter are disposed with the ratio of 1:2:1 in number.

Likewise, in the N-divided pixel unit 103d of a configuration of the present technology, an A-color filter 117d-UL, B-color filters 117d-UR and 117d-DL and a C-color filter 117d-DR are disposed. That is, in the N-divided pixel unit 103d of a configuration of the present technology, the A-color filter, the B-color filters and the C-color filter are disposed with the ratio of 1:2:1 in number. The C-color filter is a filter which transmits the light of the wavelength band of the C-color which is different from the wavelength bands of the wavelength bands of A-color and B-color.

In the N-divided pixel unit 101d of a general configuration, a blue color filter 115d is disposed. In the N-divided pixel unit 102d of a general configuration, a red color filter 116d is disposed.

Figure 16:
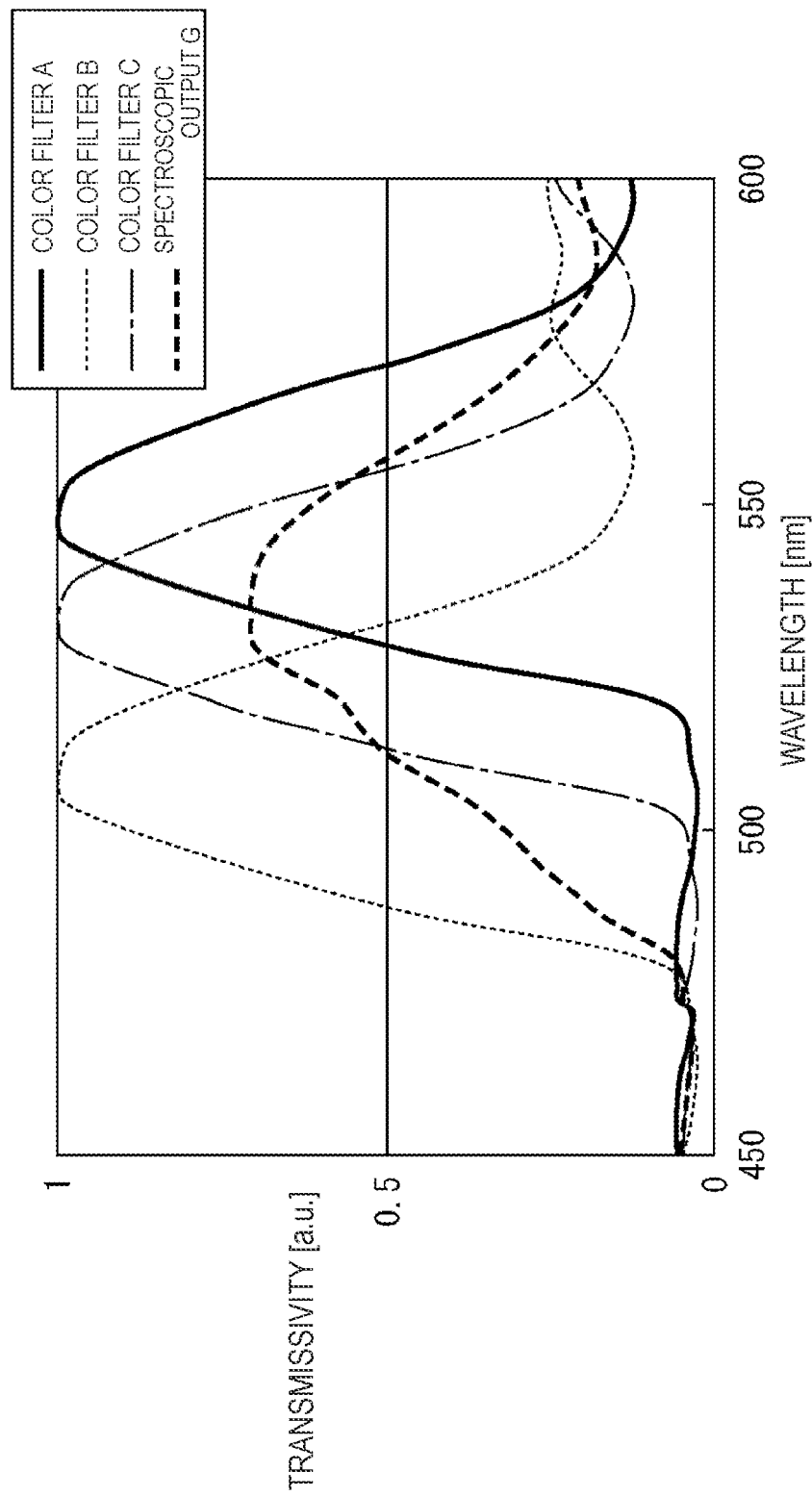
FIG. 16 is a diagram showing spectral characteristics of the lights output from the photodiode.

In the N-divided pixel units 100d and 103d of a configuration of the present technology as described above, the spectral characteristic of the light output from the photodiode is a composition result of the spectral characteristics of the A-color filter, the B-color filter and the C-color filter as shown in FIG. 16.

FIG. 16 is a diagram showing spectral characteristics of the lights output from the photodiodes in the N-divided pixel units 100d and 103d of a configuration of the present technology. In FIG. 16, the vertical axis represents the transmissivity; and the horizontal axis represents the wavelength.

As shown in FIG. 16, the A-color filter disposed in the N-divided pixel units 100d and 103d of a configuration of the present technology has such characteristic that the transmissivity is the highest in a range of wavelength of 550 nm as indicated with a solid line. The B-color filter disposed in the N-divided pixel units 100*d* and 103*d* of a configuration of the present technology has such characteristic that the transmissivity is the highest in a range of wavelength of 510 nm as indicated with a dotted line. The C-color filter disposed in the N-divided pixel units 100*d* and 103*d* of a configuration of the present technology has such characteristic that the transmissivity is the highest in a range of wavelength of 530 nm as indicated with a chain line.

In this case, the spectral characteristic of the light which enters the photodiode disposed in the N-divided pixel units 100*d* and 103*d* of a configuration of the present technology is a composition result of the characteristics of the A-color filter, the B-color filter and C-color filter; i.e., a characteristic of spectroscopic output G indicated with a dotted line in FIG. 16. Therefore, in the N-divided pixel units 100*d* and 103*d* of a configuration of the present technology, an electrical signal of a level corresponding to the spectroscopic output G is output from the photodiode.

The disposition of the color filters shown in FIG. 15 can be applied likely also in the single pixel unit of a configuration of the present technology. In this case, in the single pixel unit of a configuration of the present technology, the spectral characteristic of the light output from the photodiode is, same as FIG. 16, the characteristic of spectroscopic output G. Therefore, in the single pixel unit of a configuration of the present technology also, an electrical signal of a level corresponding to the spectroscopic output G is output from the photodiode.

As described above, with the pixel unit of a configuration of the present technology, by changing the number and type of the disposed plural color filters, a new spectral characteristic can be created.

The combination of the plural color filters disposed in the pixel unit of a configuration of the present technology is not limited to the green color filter, the red color filter and blue color filter; but color filters which transmit the light of an arbitrary wavelength band may be combined. For example, a white-color filter which transmits the lights in every wavelength bands may be combined. As for the white-color filter, for example, Japanese Unexamined Patent Application Publication No. 2009-296276 teaches a white-color filter.

The pixel unit of a configuration of the present technology may be disposed with a color filter which transmits, for example, infrared light or ultraviolet light. Referring to FIG. 17, a description will be made on an N-divided pixel unit of a configuration of the present technology in which color filter which transmits infrared light is disposed below.

[N-Divided Pixel Unit of a Configuration of the Present Technology Disposed with an Infrared Color Filter]

FIG. 17 illustrates an example of a configuration of an N-divided pixel unit of a configuration of the present technology disposed with an infrared color filter.

Upper figure in FIG. 17 is a top view of a group of N-divided pixel units 250, 252 and 253 of a configuration of the present technology and an N-divided pixel unit 251 of a general configuration.

In the N-divided pixel unit 250 of a configuration of the present technology, a red color filter is replaced with an I-color filter and a J-color filter. That is, in the N-divided pixel unit 250 of a configuration of the present technology, I-color filters 262-UL and 262-DR, and J-color filters 262-UR and 262-DL are disposed. Each of the four color filters is provided with the transfer gate 210. Also, in a central portion of the four color filters, the common FD section 211 is disposed.

Here, referring to FIG. 18, a description is made on the spectral characteristics of the I-color filter and the J-color filter.

FIG. 18 is a diagram showing the spectral characteristics of the I-color filter and the J-color filter. In FIG. 18, the vertical axis represents the transmissivity; and the horizontal axis represents the wavelength.

The I-color filter has such characteristic that the transmissivity is the highest at a wavelength of around 600 nm as indicated with a solid line. The J-color filter has such characteristic that the transmissivity is the highest at a wavelength of around 800 nm as indicated with a solid line. As described above, the I-color filter and the J-color filter are color filters that transmit the lights within a wavelength band (about 700 to 1000 nm) in which a general infrared color filter transmits the lights.

Returning to FIG. 17, in the N-divided pixel unit 251 of a general configuration, four blue color filters 265-UL, 265-UR, 265-DL and 265-DR are disposed. Each of the four blue color filters is provided with the transfer gate 210. In a central portion of the four blue color filters, the common FD section 211 is disposed.

In the N-divided pixel unit 252 of a configuration of the present technology, the green color filter is replaced with the A-color filter and the B-color filter. In the N-divided pixel unit 252 of a configuration of the present technology, A-color filters 266-UL and 266-DR, and B-color filters 266-UR and 266-DL are disposed. Each of the four color filters is provided with the transfer gate 210. Also, in a central portion of the four color filters, the common FD section 211 is disposed.

In the N-divided pixel unit 253 of a configuration of the present technology, J-color filters 267-UL and 267*b*-DR, and I-color filters 267-UR and 267-DL are disposed. Each of the four color filters is provided with the transfer gate 210. Also, in a central portion of the four color filters, the common FD section 211 is disposed.

The example in FIG. 17 shows the N-divided pixel units 250 and 252 in which the red color filter is replaced with the I-color filter and the J-color filter, and the N-divided pixel unit 252 in which the green color filter is replaced with the A-color filter and the B-color filter. Like this, with respect to plural types of pixel units, plural color filters may be disposed.

Figures at the lower-left and at the lower-right in FIG. 17 are a cross-sectional view respectively taken along a line L-L' on the N-divided pixel unit 252 and N-divided pixel unit 253 of a configuration of the present technology.

As shown at the lower-left in FIG. 17, electrical signals of different levels each corresponding to the amount of the received light at the A-color filters 266-UL and 266-DR, and the B-color filters 266-UR and 266-DL in the N-divided pixel unit 252 of a configuration of the present technology are transferred to the transfer gate 210 respectively, and then transferred to the common FD section 211. All electrical signals are added in the common FD section 211 and output therefrom.

Also, as shown at the lower-right in FIG. 17, electrical signals of different levels each corresponding to the amount of the received light at J-color filters 267-UL and 267-DR, and the I-color filters 267-UR and 267-DL in the N-divided pixel unit 253 of a configuration of the present technology are transferred to the transfer gate 210 respectively, and then transferred to the common FD section 211. All electrical signals are added in the common FD section 211 and output therefrom.

Likewise, in the N-divided pixel unit 250 of a configuration of the present technology and the N-divided pixel unit 251 of general configuration, in the common FD section 211 all electrical signals are added and a resultant signal is output therefrom.

As described above, in the N-divided pixel units 250, 252 and 253 of a configuration of the present technology, and the N-divided pixel unit 251 of a general configuration, all of the electrical signals from the photodiodes are added and then output therefrom. However, as described above, each of the electrical signals from the N photodiodes may be separately output as one electrical signal directly to the image signal reading section at the downstream (for example, the image signal reading section 533 shown in FIG. 20, which will be described below).

For example, each of the electrical signals from the photodiodes of the N-divided pixel units 250 and 253 of a configuration of the present technology in which two different I-color filter and J-color filter, which transmits infrared light are disposed, may be directly used for signal processing in the image processing section at the downstream. In this case, when a light from a single light source such as a white light enters the photodiodes of the N-divided pixel units 250 and 253 of a configuration of the present technology, two different outputs can be obtained from the infrared light range. Further, in the N-divided pixel units 250 and 253 of a configuration of the present technology, since plural color filters are included in one pixel unit, the resolution is ensured.

Therefore, an imaging apparatus mounted with the image sensor configured including the N-divided pixel units 250 and 253 of a configuration of the present technology is applicable, for example, to a medical device and the like used for analyzing live body information such as hemoglobin.

[Application to Medical Devices]

FIG. 19 illustrates an example of a configuration of a live body information obtaining system, in which an imaging apparatus including an image sensor constituted of the N-divided pixel unit of a configuration of the present technology is applied.

A live body information obtaining system 300 shown in FIG. 19 is a system in which an imaging apparatus obtains images of a live body utilizing the light passing therethrough to analyze the obtained images.

The live body information obtaining system 300 radiates a ray of light, which is emitted from a single light source provided to a light emitting section 314 attached to a support section 312 of a base 311, to a part of the live body, for example, a finger 320 which is inserted through an insertion port 313 as shown in FIG. 19. The live body information obtaining system 300 takes pictures of the finger 320 as the object with a camera 330 supported by the support section 315 of the base 311. The camera 330 includes a lens section 341, a housing 342, and an image processing section 343. The live body information obtaining system 300 analyzes the images taken by the camera 330 in the image processing section 343.

In the housing 342 of the camera 330, an image sensor constituted of an N-divided pixel unit of a configuration of the present technology is mounted. Therefore, even when the pictures of the object are taken using the light of a single light source emitted from the light emitting section 314, the camera 330 can output two different image signals which are different from each other in the infrared light range. Therefore, by analyzing the live body information using these outputs, the accuracy of the analysis is expected to be enhanced.

For example, the output values in an infrared light range may used for blood tests. That is, oxidation and deoxidation of hemoglobin in a blood can be analyzed using the output values in the infrared light range. At this time, output values of two sets of different wavelengths in the infrared light range are used. In known technology (for example, Japanese Patent No. 2932644), two sets of light are radiated to obtain output values of two different wavelengths. However, even when a single color light is used, the technique of the present technology is capable of obtaining two or more of output values from the pixel unit. Thus, the technique of the present technology is applicable to blood analysis or the like.

As described above, the technique of the present technology is capable of creating new spectral characteristics, which are difficult to obtain with the spectral characteristic of materials of color filters. Therefore, in the medical or industrial field for example, even when a special spectral characteristic, which is out of the spectral characteristic in a visual range of mankind, is needed, the pixel unit of a configuration of the present technology is capable of optimally controlling the spectral characteristic to be suitable for the purpose of application. Further, by controlling the spectral characteristic, the S/N ratio and the color reproducibility are enhanced.

Moreover, the technique of the present technology is capable of optimally designing a pixel unit suitable for the purpose of application. Therefore, even when, for example, it is difficult to divide the photodiode due to miniaturization of pixel unit, by using the technique of the present technology described referring to FIGS. 3, 4 and 10 etc, optimal pixel unit can be designed suitably for the purpose of application. Also, for example, for increasing the degree of freedom of application by setting the gain and signal processing, optimal pixel unit suitable for the purpose of application can be designed by using the technique of the present technology described referring to FIG. 11 or later.

Moreover, since the technique of the present technology increases the degree of freedom and controllability of the spectral characteristics, the light source can be easily estimated. That is, the technique of the present technology is capable of creating new spectral characteristics usable for estimating the light source in addition to the spectral characteristics of pixel values of R-pixel, G-pixel and B-pixel. Accordingly, a new light source such as white LED can be easily estimated.

[Imaging Apparatus]

FIG. 20 is a block diagram showing an example of a configuration of an imaging apparatus on which an image sensor which is configured including the above-described pixel unit of a configuration of the present technology; i.e., an imaging apparatus to which the present technology is applied.

As shown in FIG. 20, an imaging apparatus 500 includes a lens section 511, an image sensor 512, an operation section 513, a control section 514, an image processing section 515, a display section 516, a codec processing section 517 and a recording section 518.

The lens section 511 adjusts the focus to an object, concentrates the light from a focused position, and supplies the light to the image sensor 512.

The image sensor 512 is configured including a filter section 531 and a pixel section 532, and an image signal reading section 533.

The filter section 531 and the pixel section 532 constitute a group of plural pixel units to which the present technology is applied. That is, from view point of the pixel unit, the on-chip lens and the color filter constitute a part of the filter section 531. The photodiode constitutes a part of the pixel section 532. In other word, a group of the on-chip lens and the color filter included in each pixel unit constitutes the filter section 531. A group of the photodiodes included in each pixel unit constitutes the pixel section 532.

The pixel section 532 receives the light entering through the lens section and the filter section 531, and then converts the light into electric signal based on the control by the image signal reading section 533 and outputs a voltage signal (analog signal) corresponding to the intensity of the light.

That is, the image signal reading section 533 reads the analog signal of each pixel unit from the pixel section 532 as the image signal and performs A/D (Analog/Digital) conversion to obtain digital image signal, and supplies the same to the image processing section 515. Here, when one pixel unit includes plural small pixels, the image signal reading section 533 amplifies and/or adds pixel signal from each small pixel before or after the A/D conversion upon the necessity to generate pixel signal of pixel unit.

The operation section 513 is configured including, for example, JogDial (trademark), keys, buttons or touch panel and the like. Receiving operation inputs made by a user, the operation section 513 supplies signals to the control section 714 corresponding to the operation input.

The control section 514 controls the lens section 511, the image sensor 512, the image processing section 515, the display section 516, the codec processing section 517 and the recording section 518 based on the signals corresponding to the operation input made by the user through the operation section 513. For example, the control section 514 controls the image sensor 512 to switch the output manner of the level of electrical signal from each of the N photodiodes in the N-divided pixel unit of a configuration of the present technology.

The image processing section 515 performs signal processing or various image processing such as, for example, white balance adjustment, de-mosaic processing, matrix processing, gamma correction and YC conversion on the image signals supplied from the image sensor 512, and supplies the same to the display section 516 and the codec processing section 517.

The display section 516 is configured as, for example, a liquid crystal display and displays images of the object based on the image signals from the image processing section 515.

The codec processing section 517 performs a predetermined coding processing on the image signals from the image processing section 515 and supplies the image data obtained as a result of the coding processing to the recording section 518.

The recording section 518 recodes the image data from the codec processing section 517. The image data recorded in the recording section 518 is read by the image processing section 515 upon the necessity and is supplied to the display section 516, and corresponding image is displayed.

The configuration of the imaging apparatus which includes a solid imaging device to which the present technology is applied is not limited to the above, but another configuration may be employed.

The configuration, which has been described as a one device (or processing section) in the above description, may be configured including plural devices (or processing sections). Contrarily, the configuration, which has been described as plural devices (or processing sections) in the above description, may be configured as an integrated device (or processing section). Needless to say that each of the devices (or processing sections) may be configured including additional configuration other than that described above. When the configuration and the operation of the entire system are substantially identical, a part of the configuration of a device (or processing section) may be included in a configuration of other device (or other processing section). That is, the embodiment of the present technology is not limited to the above-described embodiments, but various modifications are conceivable within a range of the sprit of the present technology.

Additionally, the present technology may also be configured as below.

(1) An image sensor including:
a pixel unit,
the pixel unit including
a photodiode,
a first color filter and a second color filter each disposed in a different position on a plane above the photodiode, and
a first on-chip lens disposed over the first color filter and a second on-chip lens disposed over the second color filter.

(2) The image sensor according to (1), wherein
each of the first color filter and the second color filter has a spectral characteristic different from each other.

(3) The image sensor according to (1) or (2), wherein
the pixel unit outputs an electrical signal of a level corresponding to a composition result of the spectral characteristics of the first color filter and the second color filter.

(4) The image sensor according to any one of (1) to (3), wherein
the photodiode includes a first photodiode disposed below the first color filter and a second photodiode disposed below the second color filter, and
electrical signals output from the pixel unit having levels corresponding to the respective spectral characteristics of the first color filter and the second color filter are added.

(5) The image sensor according to any one of (1) to (4), wherein
the pixel unit further includes a common floating diffusion that adds electrical signals output from each of the first photodiode and the second photodiode.

(6) The image sensor according to any one of (1) to (5), wherein
each of the electrical signals output from the first photodiode and the second photodiode is amplified by an individually preset gain.

(7) The image sensor according to any one of (1) to (6), wherein
each of the first photodiode and the second photodiode is individually preset with a charge accumulating time.

(8) The image sensor according to any one of (1) to (7), wherein
each of the first color filter and the second color filter has a characteristic to transmit infrared light.

(9) The image sensor according to any one of (1) to (8), wherein
the pixel unit includes
a group of color filters which includes one or more color filters in addition to the first color filter and the second color filter, and
a group of on-chip lenses which includes one or more on-chip lenses in addition to the first on-chip lens and the second on-chip lens, the one or more on-chip lenses being disposed over the one or more color filters in addition to the first color filter and the second color filter.

(10) The image sensor according to any one of (1) to (9), wherein
the pixel unit outputs an electrical signal of a level corresponding to a composition result of the respective spectral characteristics of the color filter group.

(11) The image sensor according to any one of (1) to (10), wherein
the photodiode is constituted of a photodiode group each disposed below the color filter group, and electrical signals output from the pixel unit each having a level corresponding to a spectral characteristic of the color filter group are added.

(12) The image sensor according to any one of (1) to (11), wherein
the pixel unit further includes a common floating diffusion that adds the electrical signals each output from the photodiode groups.

(13) The image sensor according to any one of (1) to (12), wherein
each of the electrical signals output from the photodiode groups is amplified by an individually preset gain.

(14) The image sensor according to any one of (1) to (13), wherein
each photodiode group is individually preset with a charge accumulating time.

(15) The image sensor according to any one of (1) to (14), wherein
each of the color filter groups has a characteristic to transmit infrared light.

(16) The image sensor according to any one of (1) to (15), wherein
a waveguide is formed above the photodiode.

(17) The image sensor according to any one of (1) to (16), wherein
the photodiode has a plurality of output modes which are selectively switchable through an inner or outer control of the image sensor.

(18) An imaging apparatus mounted with an image sensor including a pixel unit,
the pixel unit including
a photodiode,
a first color filter and a second color filter each disposed in a different position on a plane above the photodiode, and
a first on-chip lens disposed over the first color filter and a second on-chip lens disposed over the second color filter.

(19) A live body imaging apparatus including an imaging apparatus mounted with an image sensor including a pixel unit,
the pixel unit including
a photodiode,
a first color filter and a second color filter each disposed in a different position on a plane above the photodiode, and
a first on-chip lens disposed over the first color filter and a second on-chip lens disposed over the second color filter,
wherein the imaging apparatus takes a picture of a live body as an object.

The present technology is applicable to an image sensor or an imaging apparatus.

The present disclosure contains subject matter related to that disclosed in Japanese Priority Patent Application JP 2011-183303 filed in the Japan Patent Office on Aug. 25, 2011, the entire content of which is hereby incorporated by reference.

What is claimed is:

1. An image sensor comprising:
a pixel unit; the pixel unit including:
a first on-chip lens disposed over the first color filter and a second on-chip lens disposed over the second color filter, wherein a spectral response of the first color filter is different than a spectral response of the second color filter, and
wherein an electrical signal output from the pixel unit is a result of a combination of spectral characteristics of the first and second color filters.

2. The image sensor according to claim 1, wherein the pixel unit outputs an electrical signal of a level corresponding to a composition result of the spectral characteristics of the first color filter and the second color filter.

3. The image sensor according to claim 1, wherein: the photodiode includes a first photodiode disposed below the first color filter and a second photodiode disposed below the second color filter, and electrical signals output from the pixel unit having levels corresponding to the respective spectral characteristics of the first color filter and the second color filter are added.

4. The image sensor according to claim 3, wherein the pixel unit further includes a common floating diffusion that adds electrical signals output from each of the first photodiode and the second photodiode.

5. The image sensor according to claim 3, wherein each of the electrical signals output from the first photodiode and the second photodiode is amplified by an individually preset gain.

6. The image sensor according to claim 3, wherein each of the first photodiode and the second photodiode is individually preset with a charge accumulating time.

7. The image sensor according to claim 1, wherein each of the first color filter and the second color filter has a characteristic to transmit infrared light.

8. The image sensor according to claim 1, wherein the pixel unit includes: a group of color filters which includes one or more color filters in addition to the first color filter and the second color filter, and a group of on-chip lenses which includes one or more on-chip lenses in addition to the first on-chip lens and the second on-chip lens, the one or more on-chip lenses being disposed over the one or more color filters in addition to the first color filter and the second color filter.

9. The image sensor according to claim 8, wherein the pixel unit outputs an electrical signal of a level corresponding to a composition result of the respective spectral characteristics of the color filter group.

10. The image sensor according to claim 9, wherein each of the color filter groups has a characteristic to transmit infrared light.

11. The image sensor according to claim 8, wherein:
the photodiode is constituted of a photodiode group each disposed below the color filter group, and
electrical signals output from the pixel unit each having a level corresponding to a spectral characteristic of the color filter group are added.

12. The image sensor according to claim 11, wherein the pixel unit further includes a common floating diffusion that adds the electrical signals each output from the photodiode groups.

13. The image sensor according to claim 11, wherein each of the electrical signals output from the photodiode groups is amplified by an individually preset gain.

14. The image sensor according to claim 11 wherein each photodiode group is individually preset with a charge accumulating time.

15. The image sensor according to claim 1, wherein a waveguide is formed above the photodiode.

16. The image sensor according to claim 1, wherein the photodiode has a plurality of output modes which are selectively switchable through an inner or outer control of the image sensor.

17. The image sensor of claim 1, further comprising:
a plurality of pixel units, wherein a first portion of the plurality of pixel units include a single photodiode and first and second color filters, and wherein a second portion of the plurality of pixels include a single photodiode and a single color filter.

18. An imaging apparatus mounted with an image sensor comprising a pixel unit, the pixel unit including:
- at least a first photodiode;
- a first color filter and a second color filter each disposed in a different position on a plane above the at least a first photodiode;
- a first on-chip lens disposed over the first color filter and a second on-chip lens disposed over the second color filter, wherein a spectral response of the first color filter is different than a spectral response of the second color filter, and wherein an electrical signal output from the pixel unit is a result of a combination of spectral characteristics of the first and second color filters.

19. A live body imaging apparatus including an imaging apparatus mounted with an image sensor comprising a pixel unit, the pixel unit including:
- at least a first photodiode;
- a first color filter and a second color filter each disposed in a different position on a plane above the at least a first photodiode; and
- a first on-chip lens disposed over the first color filter and a second on-chip lens disposed over the second color filter, wherein a spectral response of the first color filter is different than a spectral response of the second color filter, and wherein an electrical signal output from the pixel unit is a result of a combination of spectral characteristics of the first and second color filters, wherein,
- the imaging apparatus takes a picture of a live body as an object.

* * * * *